United States Patent
Kreymann et al.

(10) Patent No.: US 11,344,656 B2
(45) Date of Patent: May 31, 2022

(54) METHODS AND SYSTEMS FOR REMOVING CARBON DIOXIDE

(71) Applicant: ADVITOS GMBH, Munich (DE)

(72) Inventors: Bernhard Kreymann, Munich (DE); Christoph Hüsstege, Munich (DE)

(73) Assignee: ADVITOS GMBH, Munich (DE)

( * ) Notice: Subject to any disclaimer, the term of this patent is extended or adjusted under 35 U.S.C. 154(b) by 0 days.

(21) Appl. No.: 16/615,057

(22) PCT Filed: May 22, 2018

(86) PCT No.: PCT/IB2018/053589
§ 371 (c)(1),
(2) Date: Nov. 19, 2019

(87) PCT Pub. No.: WO2018/215918
PCT Pub. Date: Nov. 29, 2018

(65) Prior Publication Data
US 2020/0164127 A1    May 28, 2020

Related U.S. Application Data

(60) Provisional application No. 62/509,266, filed on May 22, 2017.

(51) Int. Cl.
*A61M 1/16* (2006.01)
*B01D 61/24* (2006.01)

(52) U.S. Cl.
CPC ........ *A61M 1/1609* (2014.02); *A61M 1/1676* (2014.02); *A61M 1/1696* (2013.01);
(Continued)

(58) Field of Classification Search
CPC .............. A61M 1/1609; A61M 1/1676; A61M 1/1696; A61M 2202/0225;
(Continued)

(56) References Cited

U.S. PATENT DOCUMENTS 3,846,236 A    11/1974   Updike et al.
3,953,329 A     4/1976   Updike
(Continued)

FOREIGN PATENT DOCUMENTS

CN        1120439 A      4/1996
CN      101883594 A     11/2010
(Continued)

OTHER PUBLICATIONS

A guide for the preparation and use of buffers in biological systems by Calbiochem, Date unknown.*
(Continued)

*Primary Examiner* — Krishnan S Menon
(74) *Attorney, Agent, or Firm* — Medler Ferro Woodhouse & Mills

(57) ABSTRACT

Systems and methods suitable for extracorporeal lung support are provided that expose blood, across a semipermeable membrane, to a dialysis liquid. The dialysis liquid features a buffering agent and has a high buffering capacity for $H^+$ ions. Carbon dioxide, bicarbonate and hydrogen cations are transported across a semipermeable membrane into the dialysis liquid. The dialysis fluid may be recycled and repeatedly used, and its pH may be adjusted, and other fluids added to it. Certain substances may be removed from the blood, and the amount of these substances removed from the blood may be substantially automatically or substantially continuously monitored or quantified. The systems and methods are suitable for treating or preventing respiratory acidosis, metabolic acidosis, and diseases featuring lung malfunction, kidney malfunction, or liver malfunction.

19 Claims, 7 Drawing Sheets

(52) U.S. Cl.
CPC ... *B01D 61/243* (2013.01); *A61M 2202/0225* (2013.01); *A61M 2250/00* (2013.01)

(58) Field of Classification Search
CPC ............ A61M 2250/00; A61M 1/1654; A61M 1/287; B01D 61/243
See application file for complete search history.

(56) References Cited

U.S. PATENT DOCUMENTS

| | | |
|---|---|---|
| 4,375,414 A | 3/1983 | Strahilevitz |
| 4,663,049 A | 5/1987 | Kolff et al. |
| 4,769,132 A | 9/1988 | Patono |
| 5,561,115 A | 10/1996 | Tenold |
| 5,744,042 A | 4/1998 | Stange et al. |
| 6,264,680 B1 | 7/2001 | Ash |
| 6,569,112 B2 | 5/2003 | Strahilevitz |
| 6,602,502 B1 | 8/2003 | Strahilevitz |
| 6,821,431 B2 | 11/2004 | Collins et al. |
| 7,112,273 B2 | 9/2006 | Weigel et al. |
| 7,435,342 B2 | 10/2008 | Tsukamoto |
| 7,455,771 B2 | 11/2008 | Kreymann |
| 7,670,491 B2 | 3/2010 | Callan et al. |
| 8,377,308 B2 | 2/2013 | Kreymann et al. |
| 8,480,899 B2 | 7/2013 | Kreymann |
| 8,574,438 B2 | 11/2013 | Kreymann et al. |
| 9,039,896 B2 | 5/2015 | Kreymann |
| 9,248,112 B2 | 2/2016 | Moddel et al. |
| 2002/0019603 A1 | 2/2002 | Strahilevitz |
| 2002/0158019 A1 | 10/2002 | Collins et al. |
| 2002/0187940 A1 | 12/2002 | Masuda et al. |
| 2003/0105424 A1 | 6/2003 | Karoor et al. |
| 2005/0006296 A1 | 1/2005 | Sullivan et al. |
| 2005/0082225 A1 | 4/2005 | Kreymann |
| 2010/0258503 A1 | 10/2010 | Kreymann et al. |
| 2012/0080377 A1 | 4/2012 | Jensen et al. |
| 2012/0190103 A1 | 7/2012 | Maurer |
| 2013/0087210 A1 | 4/2013 | Brandl et al. |
| 2013/0118979 A1 | 5/2013 | Kreymann et al. |
| 2015/0086969 A1 | 3/2015 | Evans et al. |
| 2015/0012271 A1 | 5/2015 | Brandl et al. |
| 2015/0335807 A1 | 11/2015 | Kellum, Jr. et al. |

FOREIGN PATENT DOCUMENTS

| | | |
|---|---|---|
| CN | 102138932 A | 8/2011 |
| CN | 102421431 A | 4/2012 |
| CN | 102940886 A | 2/2013 |
| CN | 104394902 A | 3/2015 |
| EP | 0615780 A1 | 9/1994 |
| EP | 0976759 A2 | 2/2000 |
| EP | 1649883 A1 | 4/2006 |
| EP | 1867354 A2 | 12/2007 |
| EP | 2019296 A1 | 1/2009 |
| EP | 2214752 A1 | 8/2010 |
| FR | 2651438 A1 | 3/1991 |
| GB | 1484642 A | 9/1977 |
| JP | 2000-038348 A | 2/2000 |
| JP | 2000-72658 A | 7/2000 |
| JP | 2011-505209 A | 2/2011 |
| JP | 2012-228285 A | 11/2012 |
| WO | 8400689 A1 | 3/1984 |
| WO | 9421363 A1 | 9/1994 |
| WO | 01/51185 A1 | 7/2001 |
| WO | 2002/049693 A2 | 6/2002 |
| WO | 2003/094998 A1 | 11/2003 |
| WO | 2004/066121 A2 | 8/2004 |
| WO | 2004/069311 A1 | 8/2004 |
| WO | 2005/035023 A1 | 4/2005 |
| WO | 2009/071103 A1 | 11/2009 |
| WO | 2013/144793 A1 | 10/2013 |
| WO | 2014113740 A1 | 7/2014 |
| WO | 2014/160370 A1 | 10/2014 |
| WO | 2015/074973 A1 | 5/2015 |
| WO | 2017084683 A1 | 5/2017 |
| WO | 2017085291 A1 | 5/2017 |
| WO | 2018215918 A1 | 11/2018 |

OTHER PUBLICATIONS

International Search Report and Written Opinion in corresponding International Application No. PCT/IB2018/053589, dated Nov. 29, 2018, 15 pages.
Al-Chalabi, Ahmed et al., "Evaluation of the Hepa Wash Treatment in Pigs with Acute Liver Failure," BMC Gastroenterology, Biomed Central Ltd., London, GB, vol. 13, No. 1, May 13, 2013 (May 13, 2013), 10 pages.
Benjamin Struecker et al: "Liver support strategies: cutting-edge technologies", Nature Reviews/Gastroenterology & Hepatology, vol. 11, No. 3, Oct. 29, 2013 (Oct. 29, 2013), pp. 166-176, XP055323390, US ISSN: 1759-5045, DOI: 10.1038/nrgastro.2013.204 the whole document figure 1.
Daugirdas, et al., Handbook of Dialysis, 4th Ed., pp. 59-79.
Fasano et al., "The Extraordinary Ligand Binding Properties of Human Serum Albumin", Life Dec. 2005; 57(12): 787-796.
Huber et al., "First clinical experience in 14 patients treated with ADVOS: a study on feasibility, safety and efficacy of a new type of albumin dialysis", BMC Gastroenterology, vol. 17, No. 1, Feb. 16, 2017 (Feb. 16, 2017), pp. 1-11.
Jan Stange et al., Artificial Organs, 26 (2), International Society for Arlilicial Organs, "The Molecular Adsorbents Recycling System as a Liver Support System Based on Albumin Dialysis: A Summary of Preclinical Investigations, Prospective, Randomized, Controlled Clinical Trial, and Clinical Experience from 19 Centers" pp. 103-110, 2002.
J. G. O'Grady et al., Liver, Pancreas, and Biliary Tract, "Controlled Trials of Charcoal Hemoperfusion and Prognostic Factors in Fulminant Hepatic Failure", Gastroenterology 94: pp. 1186-1192, 1988.
Karla C. L. Lee et al: "Extracorporeal liver support devices for listed patients", Liver Transplantation, vol. 22, No. 6, May 26, 2016 (May 26, 2016), pp. 839-848, XP055323376, US ISSN: 1527-6465, DOI: 10.1002/lt.24396 the whole document.
Laleman et al., "Acute-on-chronic liver failure: current concepts on definition, pathogenesis, clinical manifestations and potential therapeutic interventions", Expert Review of Gastroenterology & Hepatology, vol. 5, No. 1, Aug. 2011 (Aug. 4, 2011), pp. 523-537.
Misra, "The Basics of Hemodialysis Equipment," Hemodialysis International 2005; 9: 30-36.
Nahas et al. (Guidelines for the Treatment of acidaemia with THAM, Drugs, pp. 191-224, Feb. 1998). (Year: 1998).
Nolte, Stephan H. et al., "Hemodialysis for Extracorporeal Bicarbonate/CO2 Removal (ECBicCO2R) and Apneic Oxygenation for Respiratory Failure in the Newborn," Asaio Transactions, vol. 35, No. 1, Jan. 1, 1989 (Jan. 1, 1989), 5 pages.
Peters, T. "All About Albumin: Biochemistry, Genetics, and Medical Applications," Dec. 8, 1995; New York Academic Press, Chapter 3.
Polaschegg, et al., "Hemodialysis machines and monitors, in: Replacement of Renal Function by Dialysis", 5th Ed., eds. Horl, Koch, Lindsay, Ronco, Winchester, pp. 325-449.
Russ, Martin et al., "Experimental High-vol. Hemofiltration With Predilutional Tris-Hydroxymethylaminomethane for Correction of Low Tidal Volume Ventilation-Induced Acidosis," Artificial Organs, vol. 35, No. 6, May 30, 2011 (May 30, 2011), 11 pages.
Schwarzbeck, et al., Clin Nephrol, 1977 7(3): 125-7.
Sponholz et al., "Molecular adsorbent recirculating system and single-pass albumin dialysis in liver failure-a prospective, randomised crossover studfy", Critical Care (London, England), vol. 20, Jan. 4, 2016 (Jan. 4, 2016), pp. 1-13.
Table of Acids with Kas and pKas (1 page). (Year: 2002).
Vanholder et al., "A Bench to Bedside View of Uremic Toxins," A Soc Nephrol May 2008: 19: 863-87.
Worthley (Hydrogen Ion Metabolism, Anaeth. Intens. Care, 1977 5, pp. 347-360). (Year: 1977).

* cited by examiner

METHODS AND SYSTEMS FOR REMOVING CARBON DIOXIDE

FIELD OF THE INVENTION

Systems and methods useful for extracorporeal lung support are described herein. A dialysis fluid may be provided, and carbon dioxide, bicarbonate and hydrogen cations may be efficiently transported from a biological fluid such as blood across a semipermeable membrane into the dialysis liquid. The present systems and methods are useful for treating or preventing a variety of conditions associated with the presence of undesired substances in the blood and/or with undesired blood pH such as malfunction of the lungs, kidneys or liver.

BACKGROUND OF THE INVENTION

Metabolite Transport in the Blood

One of the metabolites of the vertebrate (human or animal) body, resulting mainly from cellular respiration, is carbon dioxide ($CO_2$). In the vertebrate (human or animal) body, carbon dioxide is produced in peripheral tissues as a result of metabolic activity. In the capillaries of peripheral tissues, carbon dioxide produced in the tissues diffuses down its partial pressure gradient into the blood, mainly into the erythrocyte. In the vertebrate body, there are three major ways in which carbon dioxide is transported in the blood: (a) dissolved $CO_2$ (carbon dioxide is much more soluble in blood than oxygen), (b) bound to blood proteins, such as hemoglobin and plasma proteins, and (c) in the form of the ion pair: bicarbonate ions and $H^+$ ions. In a resting adult human, approximately 10 mmol $CO_2$ are produced per minute. Further, every minute approximately 8 mmol $H^+$ ions are produced in the erythrocytes (approximately 15,000 mmol/day). The kidney typically accounts for a removal of approximately 100 mmol $H^+$ ions/day. This is calculated based on the amount of blood in an adult human being (5 l), 10 mmol $CO_2$ are loaded per minute into 5 l of blood, i.e. 2 mmol $H^+$ ions per 1 of blood. On the molecular level, protein-bound carbon dioxide (b) reversibly binds to blood proteins, such as hemoglobin and plasma proteins, by associating with amino groups of blood proteins, e.g. hemoglobin, to form carbamino proteins, e.g. carbaminohemoglobin. Carbon dioxide does not typically bind to iron, as oxygen does, but to amino groups of the hemoglobin protein and to amino groups on the polypeptide chains of other blood proteins, particularly plasma proteins. Bicarbonate ions (c), originate from carbon dioxide which, following its entry into red blood cells (erythrocytes), combines with water to form carbonic acid ($H_2CO_3$). This reaction is mainly catalyzed by the enzyme carbonic anhydrase, which is found inter alia in red blood cells. The enzyme is also found in the lung endothelium and at other sites of the body. Carbonic acid then dissociates to form bicarbonate ions ($HCO_3^-$) and hydrogen cations:

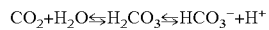

$$CO_2 + H_2O \leftrightarrows H_2CO_3 \leftrightarrows HCO_3^- + H^+$$

The reactants (educts and products) of this reaction are present in dynamic equilibrium—as qualitatively indicated by the arrows ($\leftrightarrows$) in the above equation. Addition or removal of one or more reactants (be it in vivo or in vitro) causes, by Le Chatelier's principle, a shift of the reaction, in accordance with the equilibrium. Carbonic anhydrase is not strictly required for this reaction to occur as such; however, it is important for efficient conversion.

As a result of metabolic activity, the human or animal body also produces acidic organic molecules. The acidic organic molecules are a further source of $H^+$ ions. The presence of $H^+$ ions influences the blood pH. However, within the human or animal body, fluids such as blood must be maintained within a narrow pH range, e.g. in the human body in the range of pH 7.35 to 7.45, i.e., slightly alkaline. Buffering of the blood is therefore important. When a subject suffers from a condition associated with excess amounts of $H^+$ ions, the buffering capacity of the blood is usually insufficient to maintain the blood within that pH range.

In general, hydrogen cations which are formed when carbonic acid dissociates into hydrogen cations and bicarbonate ions, can bind to proteins in the blood, particularly in the erythrocyte. The major intracellular hydrogen cation acceptor or buffer for binding of hydrogen cations is the protein hemoglobin. Hydrogen cations primarily bind to the histidine side chains of hemoglobin.

Bicarbonate serves a crucial biochemical role in the physiological pH buffering system. In a healthy vertebrate (human or animal) body, (a) about 5% of carbon dioxide is transported unchanged, dissolved in the plasma; (b) about 10% of carbon dioxide is transported bound to blood proteins, particularly hemoglobin and plasma proteins; and (c) the majority of carbon dioxide is transported in the form of bicarbonate ions and hydrogen cations; the latter are mainly bound to proteins.

In the respiratory organs of a healthy human or animal body, i.e. the lungs, carbon dioxide is released and thereby the partial pressure of $CO_2$ ($pCO_2$) is decreased. Normal values of $pCO_2$ in a (human) subject's arterial blood are in the range 35-45 mmHg. A $pCO_2$ of more than 45 mmHg is referred to as a "high $pCO_2$" or "increased $pCO_2$". Hypoventilation is one possible cause of high $pCO_2$. If the $pCO_2$ in a subject's arterial blood is higher than 45 mmHg, the subject may need a treatment in order to reduce $pCO_2$.

Acidosis

The term acidosis refers to an increased acidity in the mammalian body. Acidosis may be determined by measuring the pH of a subject's bodily fluids, particularly blood plasma, more particularly arterial blood plasma. In mammals, particularly humans, acidosis is characterized by a pH of arterial blood plasma below 7.35. Blood pH values of below 6.8 are usually not tolerated by a human or animal body since a pH outside this range usually results in irreversible cell damage. Thus, acidosis is characterized by a pH of arterial blood plasma of 6.8 to less than 7.35. Hemoglobin, and to a lesser extent plasma proteins, are capable of buffering the pH of the blood, e.g. an excess of hydrogen cations. The buffering of hydrogen cations minimizes the pH change of the blood as the blood traverses the tissue capillaries. However, the buffering capacity is not unlimited, and thus, acidosis can occur.

In general, subjects suffering from acidosis may be grouped into two major subgroups based upon the molecular causes of acidity in the blood plasma, namely respiratory acidosis and metabolic acidosis. In practice, there are cases of overlap between these two conditions, i.e. a given subject may suffer from any one of (i) metabolic acidosis, or (ii) respiratory acidosis, or (iii) a combination of metabolic and respiratory acidosis.

In either case, symptoms of acidosis include headache, confusion, tiredness, sleepiness, tremors, and dysfunction of the central nervous system, which may progress to coma if there is no intervention. There is therefore a need for treatment of subjects suffering from acidosis.

Metabolic acidosis, on a molecular level, is caused by an increased amount of acidic organic molecules, caused by increased production of organic acids (e.g. lactic acid) as a result of increased metabolic activity and/or by disturbances in the ability to excrete acid via the kidneys. Metabolic acidosis in chronic renal failure (CRF) is the result of a decreased ability to excrete nonvolatile acid and the reduced renal synthesis of bicarbonate, and thus an increase in hydrogen cations in the body. Organic acids can originate for example from amino acid residues of protein catabolism or from accumulation of ketoacids (ketosis) during starvation or in diabetic acidosis. In many instances, the body attempts to compensate metabolic acidosis by respiration (respiratory compensation), however, non-volatile metabolites are not excreted by this route, and affected subjects are at risk for exhaustion leading to respiratory failure. When metabolic acidosis is severe and can no longer be compensated adequately by the lungs, treatment with infusions of a buffering compound such as bicarbonate into the body may be required. The symptoms of metabolic acidosis in chronic renal failure (CRF) can also be treated by kidney dialysis. A particular format of kidney dialysis is termed hemodialysis and is based on a device that filters wastes, salts and fluid from body fluids. Hemodialysis is the most common way to treat advanced kidney failure. However, maintenance dialysis therapies are often not able to completely correct the base deficit in metabolic acidosis (reviewed e.g. by Kopple et al., *Kidney International*, 2005; 67(S95):S21-S27).

Respiratory acidosis, on a molecular level, results from a build-up of carbon dioxide in the blood due to decreased ventilation (hypoventilation). It is most often caused by malfunction of the lungs although head injuries, drugs (especially anesthetics and sedatives), and abnormalities of the central nervous system, such as brain tumors, can cause this condition. It can also occur as a compensatory response to chronic metabolic alkalosis. If respiratory acidosis persists, e.g. in cases of illnesses that compromise pulmonary function, such as late-stage emphysema and muscular dystrophy, such compensatory mechanisms as extraneous bicarbonate infusion, cannot efficiently reverse the buildup of carbon dioxide associated with uncompensated respiratory acidosis. In these cases, the use of a lung support may be indicated.

Systems for Lung Support and for Treating Respiratory Acidosis

One of the major breakthroughs in medicine was the invention and later use of mechanical ventilation for subjects suffering from respiratory failure. In Germany each year more than 240,000 subjects are mechanically ventilated with an average treatment period of 10 days. The average mortality of these subjects is about 35%. If another organ dysfunction occurs together with respiratory failure, the mortality increases to about 75%.

Mechanical ventilation is a method to mechanically assist or replace spontaneous breathing. Mechanical ventilation may involve a machine (ventilator), or the breathing may be assisted by a healthcare professional. In either case, mechanical ventilation may involve a device penetrating into the subject's body ("invasive mechanical ventilation"), i.e. either penetrating through the mouth (such as an endotracheal tube) or penetrating through the skin (such as a tracheostomy tube). There are two main methods of mechanical ventilation, namely positive pressure ventilation where a gas (e.g. air) is pushed into the trachea, and negative pressure ventilation where a patient's chest is placed into a low pressure chamber thereby causing extension of the chest, and thus sucking air into the patient's lungs. Besides all the positive effects of mechanical ventilation there are also disadvantages such as reduction in blood perfusion of internal organs, e.g. liver, by up to 30%, decrease in blood pressure, increase in intra-abdominal pressure, decrease in the excretory renal function, ventilator-induced lung injury (VILI), barotrauma, volutrauma, atelectrauma, and biotrauma, acute respiratory distress syndrome (ARDS), pneumonia, dyspnea of sedated subjects treated in an intensive care unit (ICU), weaning after about 48 h ventilation (see, e.g., Larsen and Ziegenfuß, Beatmung, Springer, Berlin Heidelberg, 2013; Schmidt et al., *Intensive Care Med.*, 2014; 40:1-10).

Some of the undesired consequences of mechanical ventilation can be addressed by extracorporeal lung support systems. These systems aim at extracorporeal blood oxygenation, or at extracorporeal blood carbon dioxide removal. Today extracorporeal membrane oxygenation (ECMO) is one of the most common treatments for extracorporeal lung support and is used to assist or replace the function of the lungs. Blood is removed from the body and introduced into a device having a membrane (porous membrane for short term treatments or a non-porous membrane for long term treatments) separating the blood from a gas phase (oxygen, or gas mixture comprising oxygen, e.g. air or oxygen-sweep gas mixture), which allows for oxygenation of the blood. Since the extracorporeal blood flow rates during ECMO are similar to the cardiac output of up to about 7 l/min, it is possible to combine ECMO with heart support, by including a pump in the system (ECLS, extracorporeal life support). As an alternative to membrane oxygenation, oxygen can be introduced directly into extracorporeal blood, e.g. by means of an oxygen (super)saturated liquid, as described in U.S. Pat. Nos. 6,344,489 and 6,607,698, the disclosures of which are herein incorporated by reference. However, extracorporeal introduction of a liquid typically increases the volume of the blood so that volume reduction prior to reintroduction of the gas-enriched blood into the human or animal body is required. Introduction of a gas-saturated or gas-supersaturated liquid increases the risk of bubble formation. In general, the presence of bubbles, particularly oxygen bubbles, can cause undesired denaturation of blood proteins so that these methods and systems require great care in order to minimize bubble formation. Alternatively, blood may be oxygenated directly without a gas exchange membrane, e.g. by injecting oxygen into the blood by means of a bubble oxygenator. This method is associated with undesired foam formation and the risk of gas embolism. This method is not suitable to treat acidosis.

Another focus of extracorporeal lung support is extracorporeal $CO_2$ removal ($ECCO_2R$). Such treatment may be indicated, for example, in case of respiratory acidosis. As reviewed by Baker et al., *J. Intens. Care Soc.*, 2012; 13: 232-236, $ECCO_2R$ systems typically rely on the use of a gas exchange membrane across which carbon dioxide diffuses out of the extracorporeal blood into a gas chamber. According to Baker et al., the AV-$ECCO_2R$ system (Novalung, Germany) is by far the most widely used $ECCO_2R$ technique. This system relies on contacting blood in an extracorporeal circuit with a gas-permeable membrane having a gas (oxygen, or gas mixture comprising oxygen) as a "sweep gas" on the other side of the membrane thereby allowing carbon dioxide gas to cross the membrane and be removed from the gas chamber by the flow of sweep gas.

WO 2010/091867 (Novalung), the disclosure of which is herein incorporated by reference, describes an apparatus for treating a biological liquid in a three-chamber system. A first chamber is suitable for receiving a biological liquid such as blood, and a second chamber, separated from the first chamber by a gas-permeable but liquid-impermeable membrane, is capable of optionally receiving a gas such as oxygen. Due to the gas permeability of the membrane, carbon dioxide gas can diffuse from the first chamber into the second chamber thus providing $ECCO_2R$, and, optionally, oxygen gas can diffuse from the second chamber into the first chamber. Thereby, an extracorporeal lung support is provided. Small molecules, such as water, can be removed from the first chamber across a liquid-permeable membrane into a third chamber.

In summary, conventional methods and apparatuses designed for extracorporeal carbon dioxide removal rely on a gas as a dialysis liquid. This three-chamber system is relatively complicated, and can be associated with a disadvantageously high flow resistance. As an alternative, Respiratory Dialysis® (ALung Technologies), is being offered commercially. This method relies on a sweep gas instead of a dialysis liquid. This method is unsuitable for adjusting the acid-base balance and/or electrolyte homeostasis of the blood, and is not suitable for traditional dialysis devices (Cove et al. *Critical Care* 2012; 16:232).

Carbonate/bicarbonate containing dialysis liquids have been described in the art (Aucella et al., *Contrib. Nephrol.* 2007; 156:287-296; Viganò et al., Ronco/Cruz (eds.): Hemodialysis—From Basic Research to Clinical Practice). However, the described liquids are characterized by relatively high bicarbonate concentrations in the range of 35 to 48 mmol. Such dialysis liquids are not suitable or adapted for removal of excess bicarbonate from the blood. Such dialysis liquids use acetic acid as a further ingredient.

For state of the art $ECCO_2R$, a lower blood flow rate than for ECMO (i.e. about 2l/min or less) is suitable. Such blood flow rates are realized, for example, in the commonly used pECLA (pump-less extracorporeal lung assist). In general, the efficiency of both blood oxygenation and blood carbon dioxide removal is dependent to the blood flow rate according to the following principles: the higher the blood flow rate, the better the oxygenation for the whole subject (e.g. patient), and the lower the blood flow rate, the better the carbon dioxide removal from the blood ($ECCO_2R$). Typically, high-flow (suitable for ECMO) refers to >2400 ml/min; mid-flow (suitable for both ECMO and $ECCO_2R$) refers to 800-2400 ml/min, and low flow (suitable for $ECCO_2R$) refers to <800 ml/min.

Liquid breathing is an alternative form of lung support in which a normally air-breathing organism breathes an oxygen-rich liquid (such as a perfluorocarbon), rather than breathing air, in methods of TLV (total liquid ventilation) or PLV (partial liquid ventilation) whereby PFC (perfluorocarbon) containing liquid is flooded into the lungs by a mechanical ventilator for transporting breathing gases such as oxygen and carbon dioxide (see, Lachmann et al., *Intensivmed. und Notfallmed.*, 1997; 34:513-526). A standard mode of application for liquid breathing has not been established yet.

According the state of the art, withdrawal of a subject's blood into an extracorporeal circuit is performed not only for the purpose of lung support (oxygenation and/or $CO_2$ removal), but alternatively for the purpose of supporting other organs such as the liver or kidney. In many instances, patients suffer from failure of multiple organs, and thus combined treatment with a lung support (e.g. ventilator) and a liver support and a kidney support (particularly dialysis, e.g. hemodialysis) may be indicated. In view of the number of devices involved, such combined treatments are relatively complicated and thus difficult to routinely employ in clinical practice.

Problems to be Solved

An object of the present invention is to provide novel systems and methods suitable for treating acidosis. It is preferred to provide a versatile method that is suitable for treating subjects suffering from respiratory acidosis, metabolic acidosis or any combination of forms of respiratory acidosis and metabolic acidosis. It is a further object of the present invention to provide an improved method of metabolite removal, particularly carbon dioxide removal, from a biological fluid such as blood in general, and from the human or animal body in particular. It is still a further object to provide an improved method for carbon dioxide removal that overcomes the disadvantages associated with blood air contact in traditional $ECCO_2R$.

It is also an object of the invention to provide a lung support with superior quantitative capabilities for lung support, for removing $CO_2$ (or alternatively or additionally for removing the $H^+$/bicarbonate ion pair) in the mmol range. It is still a further object to provide combined removal of $H^+$ and bicarbonate in superior quantities, i.e. in the mmol range. It is yet a further object to provide a method suitable for treating failure of multiple organs, including any combination of lung failure, liver failure and kidney failure, preferably with a single device. These and further objects can be achieved using the systems and methods for removing carbon dioxide from a biological liquid, particularly blood, as provided herein.

The presently described systems and methods allow correcting, treating, or preventing acidosis, facilitating breathing, and providing time to recover from acute decompensation. Further advantages of the present invention are associated with elements of the presently described systems and methods.

SUMMARY OF THE INVENTION

Described herein are systems and methods that address the objects described above and the shortcomings of prior art methods and processes. In particular, the systems and methods described herein provide advantages over conventional methods or processes for extracorporeal carbon dioxide removal which rely on gas as a dialysis liquid. The systems and methods described herein use a liquid (dialysis liquid or dialysis fluid) in a method for extracorporeal carbon dioxide removal. This method allows for effectively removing carbon dioxide from the blood, for adjusting the blood pH to a desired or normal value, and for adjusting (increasing or decreasing) the bicarbonate concentration in the blood. The pH of the dialysis fluid may be automatically and substantially continuously measured and monitored. Similarly, the amount of carbon dioxide or hydrogen ions or bicarbonate removed from the blood may be easily, substantially automatically and substantially continuously monitored and measured thereby providing for relatively smooth and easy optimization of the systems and methods described herein. Such information may be transmitted to primary care givers for optimizing patient therapy. Therefore, the systems and methods described herein enable a versatile organ support based on the needs of individual subjects. For example, the systems and methods described herein provide lung support and in many instances liver and kidney support, dependent on the function of the liver and kidneys. Further, the systems and methods described herein provide for stabilizing or normalizing the blood pH in the case of subjects suffering from an acid-base imbalance such as metabolic or respiratory acidosis. Typically, a desired or normal value of blood pH is in the range of pH 7.35 to 7.45, preferably 7.36 to 7.44, more preferably 7.37 to 7.43, more preferably 7.38 to 7.42, more preferably 7.39 to 7.41, and most preferably about 7.40. Generally, the blood pH range of pH 6.8 to pH 8.0 may be acceptable.

According to the systems and methods described herein, a suitable dialysis fluid may be characterized by the following:
(i) a pH in the range of from pH 8.0 to pH 11.0; and
(ii) featuring at least one buffering agent having a pKa value in the range of from 7.0 to 11.0;
(iii) having a buffering capacity for $H^+$ ions of about 12 mmol/$H^+$ ions or more.

Details of the buffering capacity and the pH, and other details, are described herein, and an assay for determining the buffering capacity in accordance with the present invention is described herein. Suitable buffering agents for the dialysis fluid include, for instance, Tris(hydroxymethyl)aminomethane (Tris, THAM), carbonate/bicarbonate, and water-soluble proteins such as albumin.

In general, the systems and methods described herein provide a method for removing at least one undesired substance from a biological fluid such as blood by exposing the biological fluid such as blood to a dialysis fluid across a semipermeable membrane where the dialysis fluid possesses the preferred properties described herein. Further, in general the systems and methods described herein provide a method for removing at least one undesired substance from a biological fluid such as blood by (i) introducing the biological fluid into a first chamber of a device having a first chamber and a second chamber separated by a semipermeable membrane, and (ii) introducing a dialysis fluid having the preferred properties defined herein into the second chamber of the device. The systems and methods described herein thus provide improved means for extracorporeal carbon dioxide removal and for adjusting the pH the buffering capacity of the blood. Particularly preferred and advantageous embodiments of the systems and methods described herein are provided in this description and in the enclosed claims.

In a first aspect, the invention provides a method for removing at least one undesired substance from a biological fluid featuring (a) exposing the biological fluid to a dialysis fluid across a semipermeable membrane, wherein the dialysis fluid features (i) a pH in the range from pH 8.0 to pH 11.0, (ii) at least one buffering agent having a pKa value in the range of 7.0 to 11.0, and (iii) a buffering capacity of at least 12 mmol/l for $H^+$ ions. The at least one undesired substance may be one or more of carbon dioxide ($CO_2$), hydrogen cation ($H^+$), hydrogen carbonate ($HCO_3^-$) and solvates thereof. The method may further feature (b) automatically quantifying the amount of one or more undesired substance selected from the group consisting of carbon dioxide ($CO_2$), hydrogen cation ($H^+$), hydrogen carbonate ($HCO_3^-$) and solvates thereof, removed from the biological fluid. The automatically quantifying the amount of one or more undesired substance selected from the group consisting of carbon dioxide ($CO_2$), hydrogen cation ($H^+$), hydrogen carbonate ($HCO_3^-$) and solvates thereof, removed from the biological fluid features measuring the difference in pH of the dialysis fluid prior to exposing the biological fluid to the dialysis fluid across the semipermeable membrane compared to the pH of the dialysis fluid after contacting the biological fluid across the semipermeable membrane in accordance with the buffering capacity and the flow rate. The biological fluid may be blood.

The dialysis fluid may have at least one buffering agent that may be Tris(hydroxymethyl)aminomethane (Tris, THAM), carbonate/bicarbonate and albumin. Further, the dialysis fluid may have a pH in the range of pH 8.0 to pH 9.0 and comprises (i) 10 to 40 mmol/l carbonate/bicarbonate and (ii) 10 to 60 g/l albumin. The method may further feature (c) treating the dialysis fluid, and the treating the dialysis fluid may feature exposing the dialysis fluid to one or more of (i) an adsorber, (ii) a membrane, (iii) an acidic pH, and (iv) a basic pH. Also, the treating the dialysis fluid may feature removing carbon dioxide from the dialysis fluid. In addition, the method may further feature (d) recycling the dialysis fluid.

In a second aspect, the invention provides a method for extracorporeally treating blood from a human or animal subject by (a) withdrawing blood from the vein or artery of the subject, (b) exposing the blood to a dialysis fluid across a semipermeable membrane where the dialysis fluid features (i) a pH in the range from pH 8.0 to pH 11.0, (ii) at least one buffering agent having a pKa value in the range of 7.0 to 11.0, and (iii) a buffering capacity of at least 12 mmol/l for $H^+$ ions, (c) removing at least one undesired substance from the blood, and (d) returning the blood to the subject. The at least one undesired substance may be one or more of carbon dioxide ($CO_2$), hydrogen cation ($H^+$), hydrogen carbonate ($HCO_3^-$) and solvates thereof. The method may further feature (e) automatically quantifying the amount of the one or more undesired substance selected from the group consisting of carbon dioxide ($CO_2$), hydrogen cation ($H^+$), hydrogen carbonate ($HCO_3^-$) and solvates thereof, removed from the blood, and the automatically quantifying the amount of one or more undesired substance selected from the group consisting of carbon dioxide ($CO_2$), hydrogen cation ($H^+$), hydrogen carbonate ($HCO_3^-$) and solvates thereof, removed from the blood may feature measuring the difference in pH of the dialysis fluid prior to exposing the blood to the dialysis fluid across the semipermeable membrane compared to the pH of the dialysis fluid after contacting the blood across the semipermeable membrane. The dialysis fluid may contain at least one buffering agent from among Tris(hydroxymethyl)aminomethane (Tris, THAM), carbonate/bicarbonate and albumin. Also, the dialysis fluid may have a pH in the range of pH 8.0 to pH 9.0 and contain (i) 10 to 40 mmol/l carbonate/bicarbonate and (ii) 10 to 60 g/l albumin. The method may further feature (f) treating the dialysis fluid, and the treating the dialysis fluid may feature exposing the dialysis fluid to one or more of (i) an adsorber, (ii) a membrane, (iii) an acidic pH, and (iv) a basic pH. In addition, the treating the dialysis fluid may feature removing carbon dioxide from the dialysis fluid. The method may also feature (g) recycling the dialysis fluid.

In a third aspect, the invention provides a method of treating a subject suffering from an acid/base imbalance by (a) withdrawing a biological fluid from the subject, (b) exposing the biological to a dialysis fluid across a semipermeable membrane, where the dialysis fluid features (i) a pH in the range from pH 8.0 to pH 11.0, (ii) at least one buffering agent having a pKa value in the range of 7.0 to 11.0, and (iii) a buffering capacity of at least 12 mmol/l for $H^+$ ions, (c) removing at least one undesired substance from the biological fluid, and (d) returning the biological fluid to the subject. The at least one undesired substance may be one or more of carbon dioxide ($CO_2$), hydrogen cation ($H^+$), hydrogen carbonate ($HCO_3^-$) and solvates thereof. The method may further feature (e) automatically quantifying the amount of the one or more undesired substance selected from the group consisting of carbon dioxide ($CO_2$), hydrogen cation ($H^+$), hydrogen carbonate ($HCO_3^-$) and solvates thereof, removed from the biological fluid. The automatically quantifying the amount of the one or more undesired substance selected from the group consisting of carbon dioxide ($CO_2$), hydrogen cation ($H^+$), hydrogen carbonate ($HCO_3^-$) and solvates thereof, removed from the biological fluid may feature measuring the difference in pH of the dialysis fluid prior to exposing the biological fluid to the dialysis fluid across the semipermeable membrane compared to the pH of the dialysis fluid after contacting the biological fluid across the semipermeable membrane. The dialysis fluid may contain at least one buffering agent from among Tris(hydroxymethyl)aminomethane (Tris, THAM), carbonate/bicarbonate and albumin. Also, the dialysis fluid may have a pH in the range of pH 8.0 to pH 9.0 and contain (i) 10 to 40 mmol/l carbonate/bicarbonate and (ii) 10 to 60 g/l albumin. The method may further feature (f) treating the dialysis fluid, and the treating the dialysis fluid may feature exposing the dialysis fluid to one or more of (i) an adsorber, (ii) a membrane, (iii) an acidic pH, and (iv) a basic pH. Also, the treating the dialysis fluid may feature removing carbon dioxide from the dialysis fluid. In addition, the method may further feature (g) recycling the dialysis fluid. As well, the subject suffering from the acid/base imbalance may be suffering from one or more of respiratory acidosis, metabolic acidosis, lung failure, liver failure, and kidney failure.

In a fourth aspect, the invention provides a dialysis liquid for use in any of the methods described herein or for use in treating a human or animal subject by therapy featuring (i) a pH the range from pH 8.0 to pH 11.0, (ii) at least one buffering agent having a pKa value in the range of 7.0 to 11.0, and (iii) a buffering capacity of 12 mmol/l or more for $H^+$ ions. The dialysis fluid may contain at least one buffering agent from among Tris(hydroxymethyl)aminomethane (Tris, THAM), carbonate/bicarbonate and albumin. Also, the dialysis fluid may have a pH in the range of pH 8.0 to pH 9.0 and contain (i) 10 to 40 mmol/l carbonate/bicarbonate and (ii) 10 to 60 g/l albumin.

In a fifth aspect, the invention provides a method for determining the buffering capacity of a dialysis fluid comprising substantially continuously titrating the dialysis fluid with an acid or base solution to provide the dialysis fluid a desired or optimal pH.

In a sixth aspect, the invention provides a method for substantially continuously and substantially automatically calculating the $pCO_2$ of a biological fluid comprising determining the pH and the bicarbonate concentration of a dialysis fluid present in a dialysis circuit wherein determining the pH and the bicarbonate concentration of a dialysis fluid is performed by substantially continuously titrating the dialysis fluid with an acid or base solution to provide the dialysis fluid a desired or optimal pH.

DETAILED DESCRIPTION OF THE PREFERRED EMBODIMENTS

Definitions

Figure 1:
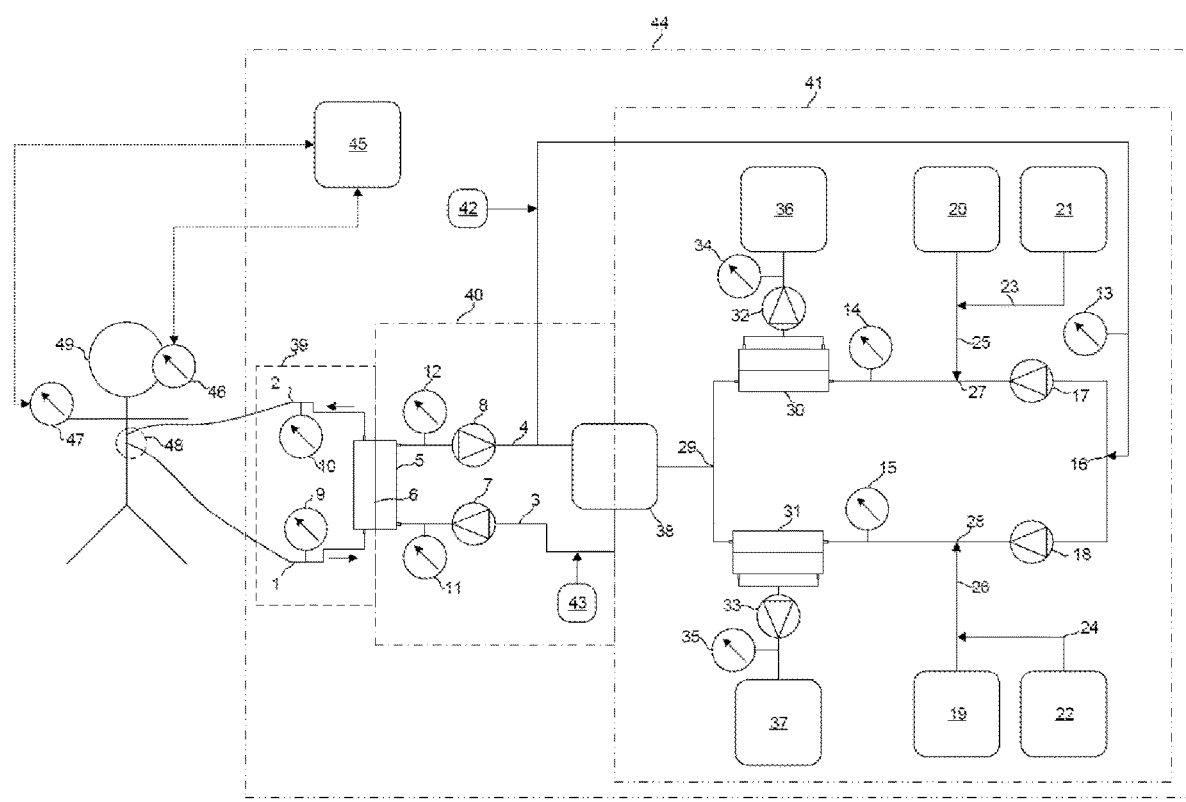
FIG. 1 provides a diagram of a dialysis system as described herein in conjunction with a human subject undergoing a treatment method as described herein.

"Comprising" as used herein provides that more items or elements than those actually listed can be present. However, in some embodiments "comprising", as used herein, is to be read more narrowly, so that it is synonymous to the terms "consisting essentially of" or "consisting of".

"Acidosis" refers to an increased acidity (i.e. an increased hydrogen cation concentration) in the blood and other body tissue. If not further specified, it typically refers to increased acidity of the blood plasma. Increased acidity typically means that the pH of arterial blood plasma is lower than 7.35, typically 6.8 to less than 7.35.

"Bicarbonate equilibrium" refers to the equilibrium between carbonic acid and bicarbonate/hydrogen cation:

$$H_2CO_3 \leftrightharpoons H^+ + HCO_3^-.$$

The equilibrium is dynamic and the dissociation occurs spontaneously (i.e. without depending on catalysis by an enzyme such as carboanhydrase).

"Buffering agent" as used herein refers to a weak acid or base which is suitable to maintain the acidity (pH) of a solution near a certain value (e.g. near the pKa value of the weak acid or base, e.g. pH=pKa±1), even if an acidic or basic compound is added. The term buffering agent can be used for solid or dissolved compounds alike. Buffering agents are typically soluble in solution, preferably aqueous solution. The function of a buffering agent is to prevent an undesired change in pH when an acidic or basic compound is added to the solution. Salts of the weak acid or base which is suitable to maintain the acidity (pH) of a solution near a certain value can also be referred to as buffering agents.

"Carboanhydrase" as used herein refers to an enzyme which catalyzes the reversible conversion of dissolved carbon dioxide to carbonic acid:

$$CO_2 + H_2O \leftrightharpoons H_2CO_3 \text{ (i.e. carbonic acid)}$$

Carboanhydrase is naturally present in red blood cells (erythrocytes) and at other sites of the human or animal body.

"Dialysis fluid" and "dialysis liquid" are used interchangeably herein.

"Erythrocytes" or red blood cells or RBCs refer synonymously to blood cells of the vertebrate organism characterized by presence of hemoglobin in the cytoplasm. RBCs take up oxygen in the lungs and release it into peripheral tissues, and take up undesired substances such as hydrogen cations and carbon dioxide in peripheral tissues and release them in the lungs. The release/uptake in peripheral tissues mainly occurs while erythrocytes pass through the capillaries of these tissues.

"Extracorporeal" refers to any process, activity, substance or device which is present or performed outside the body of a human or animal. If a process, activity, substance or device which is present or performed partially outside the body of a human or animal, the term refers to the part outside the body.

"Fluid" generally refers to a non-solid state of matter. Typically, a fluid is either a liquid or a gas.

"Hemoglobin," or Hb for short, is a protein typically present in red blood cells of the vertebrate organism. The peptide chains of hemoglobin contain numerous amino and carboxyl groups. Typically, the hemoglobin molecule is comprised of four globular protein subunits. Each subunit is composed of a protein chain (globin) which is associated with a non-protein heme group. Hemoglobin is capable of reversibly binding small molecules such as metabolites, most notably oxygen ($O_2$), hydrogen cations ($H^+$) and carbon dioxide ($CO_2$) or solvates of any of these. Typically, oxygen can reversibly bind to the heme group. In contrast, carbon dioxide can typically reversibly bind to amino groups (typically at the N-terminals and at side-chains of arginine and lysine residues in hemoglobin), which leads to the formation of carbamino groups. Hemoglobin having one or more carbamino groups is termed carbaminohemoglobin. Carbaminohemoglobin is the major contributor to the Haldane effect. Typically, carbaminohemoglobin is thought to account for about 10% of carbon dioxide transport in mammals. Finally, the carboxyl groups of hemoglobin are capable of binding, and hence buffering, hydrogen cations (such hydrogen cations are formed typically as a result of $CO_2$ dissociation and the bicarbonate equilibrium). Over the normal physiological pH range, much of the binding of hydrogen cations by hemoglobin occurs at the imidazole group of the amino acid histidine, present in the globin chain. Deoxygenated hemoglobin is a better acceptor for hydrogen cations than oxygenated hemoglobin.

"Hydrogen carbonate" or "bicarbonate" are used interchangeably to refer to an anion with the chemical formula $HCO_3^-$. Hydrogen carbonate is an intermediate form in the deprotonation of carbonic acid. It is a polyatomic anion. Unless the context dictates otherwise, the term is used herein to the hydrogen anion ($HCO_3^-$), and to any salt of bicarbonate, such as e.g. sodium bicarbonate.

"Hydrogen cation" or hydrogen ion or $H^+$ are used interchangeably herein to refer to a cationic form of atomic hydrogen. All these terms include collectively cations of all isotopes of hydrogen, particularly proton, deuteron, and triton. In aqueous solution hydrogen cations typically form solvates by addition of one or more water molecules. Such solvates are called hydroxonium ions and can be described by the general formula $H^+ (H_2O)_n$; n being an integer such as 0, 1, 2, 3, 4, or more than 4; most typically 1 or 4. The term hydrogen cation can also be used herein to refer to a hydrogen cation in solution or to solvated states a hydrogen cation.

"Metabolite" as used herein, refers to any intermediate or product of the human or animal metabolism. Particular metabolites of importance in the present invention are carbon dioxide, hydrogen carbonate and hydrogen cation.

"Oxygen" refers herein to molecular dioxygen ($O_2$) unless the context dictates otherwise. Oxygen is essential for cellular respiration in all aerobic organisms, including mammals.

"Oxygenated/deoxygenated hemoglobin" refers to the oxygenation state of hemoglobin. Since hemoglobin is typically comprised of four hemoglobin protein subunits, each of which can be oxygenated/deoxygenated reversibly, five states of oxygenation are possible: the fully deoxygenated form (all four subunits deoxygenated) is always referred to as "deoxygenated;" the fully oxygenated form (all four subunits oxygenated) is always referred to as "oxygenated." The terms "oxygenated" and "deoxygenated" are also used as relative terms herein: for example, relative to a form of hemoglobin having one subunit oxygenated, the forms having two or three or four subunits oxygenated can all be referred to as "oxygenated" hemoglobin. Conversely, the same form having one subunit oxygenated can be referred to as "oxygenated" hemoglobin relative to a form having no subunit oxygenated (i.e. all subunits deoxygenated). Deoxygenated hemoglobin is also referred to as deoxyhemoglobin. Oxygenated hemoglobin is also referred to as oxyhemoglobin. Herein, the term hemoglobin is used simultaneously for oxyhemoglobin and deoxyhemoglobin, unless the context dictates otherwise. The terms oxyhemoglobin/deoxyhemoglobin, as used herein, do not particularly require a specific quantity of hydrogen cations being bound to the oxyhemoglobin/deoxyhemoglobin protein.

$pCO_2$ refers to the partial pressure of carbon dioxide ($CO_2$) in a fluid, e.g. in blood plasma or dialysis liquid.

"Peripheral tissue" refers herein to any non-lung tissue (non-gill tissue) of a vertebrate, particularly to non-lung tissue of a mammal.

"Plasma" refers herein to blood plasma, i.e. the extracellular intravascular liquid fraction of the blood.

"pH" or pH value refers to the negative of the logarithm to base 10 of the activity of the hydrogen ion. Solutions with a pH less than 7 are acidic and solutions with a pH greater than 7 are alkaline or basic.

"pKa" is an index to express the acidity of weak acids, where pKa is defined as follows. In general, weak acids are present partially dissociated in aqueous solution according to the following equilibrium:

$$Ka = \frac{[A^-][H^+]}{[AH]}.$$

This equilibrium defines the pKa value as follows:

$$pKa = -\log_{10} Ka.$$

In general, the smaller the pKa value, the stronger the acid.

"Sodium bicarbonate" or sodium hydrogen carbonate refer interchangeably to the (water-soluble) chemical compound with the formula $NaHCO_3$ (also known as baking soda or soda or bicarbonate of soda) in any form, e.g. crystalline (e.g. anhydrous or any hydrate), or dissolved in solution, e.g. aqueous solution.

"Sodium carbonate" refers to the (water-soluble) disodium salt of carbonic acid ($Na_2CO_3$, also known as washing soda or soda ash) in any form, e.g. crystalline (e.g. anhydrous or any hydrate such as heptahydrate or decahydrate), or dissolved in solution, e.g. aqueous solution.

Solvate refers to a solute being surrounded or complexed by solvent molecules. Solvation is an interaction of a solute (e.g. an ion such as hydrogen cation ($H^+$), hydrogen carbonate ($HCO_3^-$)) with the solvent (e.g. water). In the solvated state, the solvate is typically stabilized (as opposed to a non-solvated state). Unless the context dictates otherwise, solvate preferably refers herein to a solute being solvated in water.

"Subject" or patient refers to an individual human or animal, preferably human. A subject can be healthy or suffering from at least one medical condition, disease or illness. A patient is a subject suffering from at least one medical condition, disease or illness. In the context of this specification, the term patient can designate an individual suffering from any one or more of the specific conditions disclosed herein.

The systems and methods described herein address the objects and the shortcomings of prior art methods and processes described above. In particular, the systems and methods described herein provide advantages over conventional methods or processes for extracorporeal carbon dioxide removal that rely upon gas as a dialysis liquid, by providing a liquid dialysis fluid (dialysis liquid) in a method for extracorporeal carbon dioxide removal. These systems and methods allow effectively removing carbon dioxide from the blood or adjusting the blood pH to a desired or normal value or to adjusting (increasing or decreasing) the bicarbonate concentration in the blood. Therefore, the systems and methods enable a versatile organ support based on the needs of individual subjects. For example, the systems and methods provide lung support and/or kidney support, dependent on the function of the kidney, and stabilize the blood pH in the case of subjects suffering from respiratory acidosis, e.g. by increasing the body's production of bicarbonate. Typically, a desired or normal value of blood pH lies in the range of pH 7.35 to 7.45, preferably 7.36 to 7.44, more preferably 7.37 to 7.43, more preferably 7.38 to 7.42, more preferably 7.39 to 7.41, and most preferably about 7.40. More generally, the blood pH range of pH 6.8 to pH 8.0 may be acceptable.

According to the systems and methods described herein, a suitable dialysis liquid is characterized as follows:
(i) having a pH the range from pH 8.0 to pH 11.0; and
(ii) comprising at least one buffering agent, wherein the buffering agent is characterized by at least one pKa value in the range from 7.0 to 11.0;
(iii) having a buffering capacity for $H^+$ ions which is 12 mmol/l $H^+$ ions or more.

Details of the buffering capacity and the pH, and other details, are given below. An assay for determination of the buffering capacity in accordance with the present invention is given below.

Suitable buffering agents in the dialysis liquid include in particular any one or more of the following: Tris(hydroxymethyl)aminomethane (Tris, THAM); carbonate/bicarbonate; water-soluble proteins, preferably albumin.

The systems and methods described herein thus provide (i) a process for removal of at least one undesired substance from blood, featuring exposing blood to a dialysis liquid across a semipermeable membrane, wherein the dialysis liquid has the properties or preferred properties defined herein; and (b) a process for removal of at least one undesired substance from blood, featuring: (i) introducing blood into a first chamber of a device, said device comprising a first chamber and a second chamber, wherein the first chamber and the second chamber are separated by a semipermeable membrane, (ii) introducing a dialysis liquid into a second chamber of said device, wherein the dialysis liquid being introduced into the second chamber, wherein the dialysis liquid has the properties or preferred properties defined herein.

The systems and methods described herein are suitable for extracorporeal carbon dioxide removal and/or for adjusting the pH and/or for adjusting the buffering capacity of the blood. Particular, preferred and advantageous embodiments of the systems and methods described herein are provided in this description and in the enclosed claims.

The term first chamber is generally used to refer to a chamber configured or suitable to receive blood, and the term second chamber is generally used to refer to a chamber configured or suitable to receive a dialysis liquid; typically, the first and second chamber are separated from each other by a semipermeable membrane as defined herein. Typically, no direct connection (tubing or the like) exists between the first chamber and the second chamber. Thus, only those substances which are capable of traversing the semipermeable membrane can migrate from the first chamber into the second chamber and/or from the second chamber into the first chamber.

Blood and the dialysis liquid are aqueous fluids. The term aqueous is generally used herein to refer to water or water-containing fluids, particularly but without limitation to the liquid state thereof. The term aqueous is used herein to refer to fluids, particularly liquids or liquid phases, comprising water. Typically, aqueous liquids comprise more than 50% (vol./vol.) water, and are hydrophilic. Blood and the dialysis liquid are such aqueous fluids. Thus, a fundamental difference between the systems and methods described herein and extracorporeal carbon dioxide removal methods of the prior art ($ECCO_2R$) is that the present invention employs a dialysis fluid in liquid state.

In remote technical areas, or for remote purposes (i.e. distinct from the purpose of and extracorporeal carbon dioxide removal ($ECCO_2R$)), the use of liquid dialysis fluids has been described in the prior art. In these prior art systems, the dialysis liquid is brought in proximity to extracorporeal blood, separated by a semipermeable membrane, thus allowing the transfer of the undesired substances from the blood along the concentration gradient into the dialysis liquid, and optionally of desired substances in the opposite direction. These prior art systems are directed at other purposes, i.e. kidney support and/or liver support. For example, dialysis for kidney support can be indicated in case of acidosis which can result from chronic renal failure (CRF). Such kidney support dialysis therapies are, however, generally unsuitable for aiding or substituting liver functions, i.e. for removing certain substances (particularly toxins), such as protein-bound substances (particularly toxins) from the blood. WO 03/094998 A1 (HepaWash) describes an apparatus and a method for the removal of protein-bound substances (particularly toxins) from blood, which relies on an absorber liquid which is suitable as dialysis liquid for liver dialysis, wherein the dialysis liquid comprises albumin, and may optionally comprise caffeine. This allows for binding of protein-bound toxins to the carrier albumin. These prior art systems are, however, not directed at providing a lung support, let alone an efficient removal of carbon dioxide ($CO_2$), hydrogen cation ($H^+$) and hydrogen carbonate ($HCO_3^-$). It was surprising to find that a dialysis liquid in general, and the specific dialysis liquid as defined herein in particular, is particularly suitable for the purpose of extracorporeal carbon dioxide removal, and for adjustment of bicarbonate levels. These goals can be achieved in personalized medicine, i.e. depending on the needs of an individual patient.

In general, albumin has the capacity to buffer aqueous liquids, and it is thought that certain amino acid residues of albumin (e.g. imidazole group of histidine, thiol group of cysteine) are important (Caironi et al., *Blood Transfus.*, 2009; 7(4): 259-267), and at more elevated pH values, the amino groups of lysine side chains and of the N-termini may contribute to buffering. However, the buffering capacity of albumin has traditionally been exploited in blood (where it occurs naturally in the human or animal body), and the suitability of albumin-containing liquids for extracorporeal lung support, or extracorporeal carbon dioxide removal in particular, has not been recognized or exploited in the art. Also bicarbonate is known to provide physiological pH buffering system. Bicarbonate-containing dialysis liquids, although without albumin, have been previously described in the art. Typical bicarbonate concentrations in such previous dialysis liquids range from 32 to 40 mmol/l. The systems and methods described herein are advantageous compared to such previous uses, inter alia because the buffering capacity of buffering agents with a pKa in the above-specified range, such as albumin, carbonate/bicarbonate, or Tris can be taken advantage of. Optionally, other inorganic or organic buffering agents are present. Preferably, such buffering agents have at least one pKa value in the range between 7.0 and 9.0. Suitable additional organic buffering agents include proteins, particularly water-soluble proteins, or amino acids, or Tris; and suitable additional inorganic buffering molecules include $HPO_4^{2-}/H_2PO_4^-$.

A further advantage of the systems and methods described herein is their versatility. Depending on the blood flow rates (up to 600 ml/min, or in case of two parallel devices up to 1200 ml/min), dialysis liquid flow rates (up to 2000 ml/min) and the exact dialysis liquid composition it is possible to remove between 0 and 10 mmol/min of carbon dioxide from the blood.

Diagrammatic Representation of a System Described Herein

Figure 2:
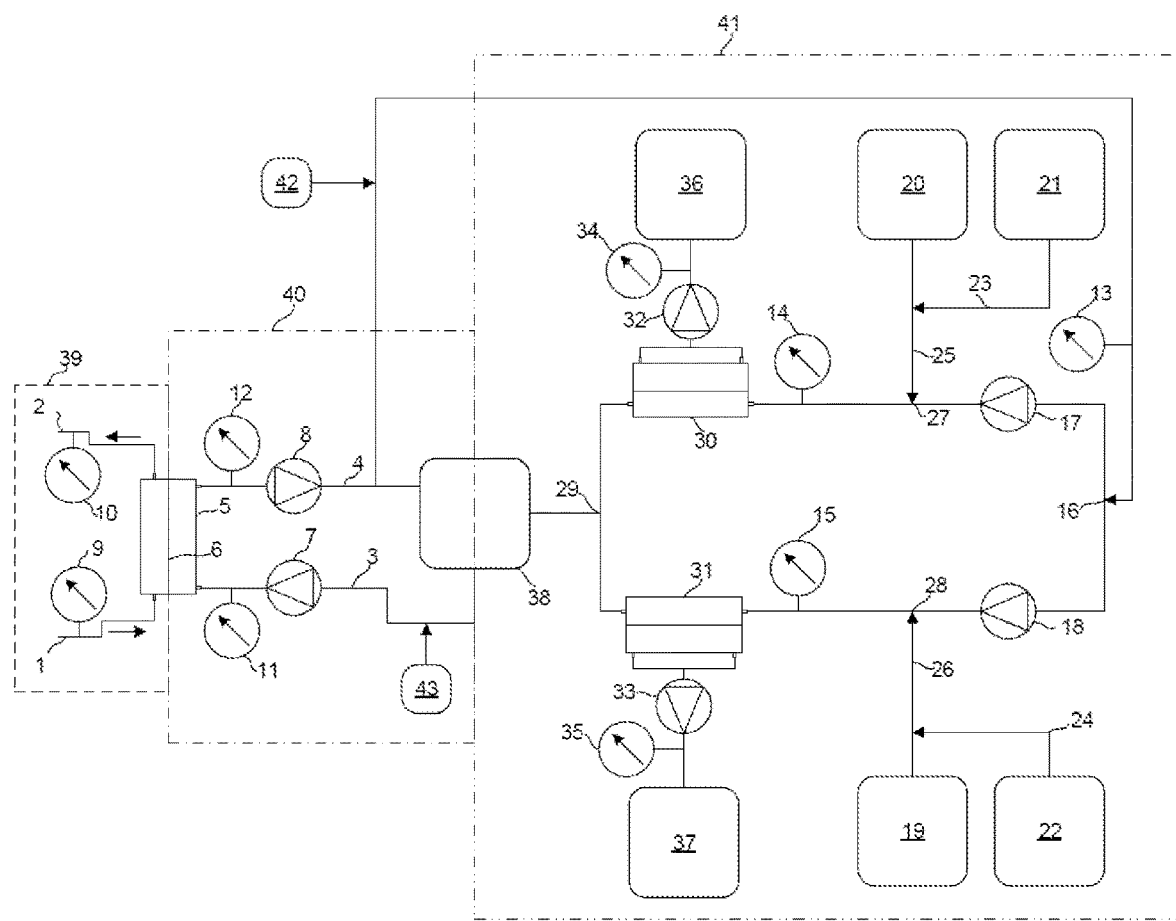
FIG. 2 provides a diagram of a dialysis system as described herein.

Referring to FIGS. 1 and 2, an input liquid to treat 1, e.g. blood, enters the dialysis system and an output liquid to treat 2, e.g. blood, exits the dialysis system. A regenerated input liquid for exchange purpose with a known buffer 3 is provided, and an output liquid for exchange purpose which will be analyzed and regenerate 4 is produced. The dialysis system features a two chamber device, e.g. a dialyzer 5, and a semipermeable membrane 6. One or more pumps 7, 8, 17, and 18 are provided at various points as needed to produce and facilitate the flow of liquids as desired. One or more sensors 9, 10 are provided to measure or monitor one or more of pH, temperature, $pCO_2$, hemoglobin concentration, oxygen saturation, and flow rate. Similarly, one or more sensors 11, 12, 13, 14, 15 are provided to measure or monitor one or more of pH, $pCO_2$, $cCO_2$, flow rate, conductivity, and temperature. A split point 16 leading to two distinct paths for the dialysis fluid contained therein is also provided. An osmosis water source or reservoir 19, 20 is provided along each of the distinct paths originating from the split point 16. Along one distinct path, an acid concentrate, e.g. HCl, 21 is provided having an acid flow way 23 that produces an acidic mixed supply solution having a known $H^+$ concentration 25 when mixed with the osmosis water source or reservoir 20. Along a second distinct path, a base concentrate, e.g. NaOH, 22 is provided having a base flow way 24 that produces a base mixed supply solution having a known $OH^-$ concentration 26 when mixed with the osmosis water source or reservoir 19. Two mixing points of fresh supply solution and recirculated solution 27, 28 are provided, one in each of the two distinct paths. Also, a neutralization or mixing zone 29 is provided downstream of the two distinct paths. Two filters 30, 31 are provided, one in each distinct path. Two waste pumps 32, 33 are provided, one in each distinct path, and one or more appropriate sensors 34, 35 may be provided downstream of the waste pumps 32, 33 for measuring one or more of pH, $pCO_2$, $cCO_2$, flow rate, conductivity, temperature, and to act as a titrator. One or more waste reservoir 36, 37 may also be provided. The dialysis system features a reservoir/buffer tank/mixing zone 38 and a circuit for the liquid to be treated 39. Likewise, the dialysis system features a circuit for the exchange and differential measurement of the exchange 40 along with a circuit for the titration and adjustment of the liquid 41. In some instances, one or more optional additional solution 42, 43 may be provided as needed or as desired.

Referring only to FIG. 1, the dialysis system as described herein 44 is represented. The dialysis system may further feature a controller, such as an electronic controller 45 that may be within or external to the dialysis system 44 as represented, one or more additional sensor 46 for measuring or monitoring one or more of $CO_2$ partial pressure or Volume %, capnography or infrared spectroscopy that may also be external to the dialysis system as represented 44, and one or more additional sensor 47 for measuring one or more of $pCO_2$, $tcpCO_2$, $SpCO_2$, $pO_2$, $tcpO_2$, $SpO_2$, pulse, or temperature that may also be external to the dialysis system as represented 44. There may then be provide connection ports 48 for effectively engaging the dialysis system 44 with a patient 49.

Blood

In the vertebrate (human or animal) body, blood is composed of blood cells and blood plasma (also referred to as "plasma"), so that the blood cells are suspended in the plasma. In the vertebrate body, the major component of plasma is water, and the major type of blood cells are erythrocytes. The systems and methods described herein are suitable for application to all types of blood from humans or animals, preferably vertebrates, preferably mammals, and most preferably humans, and are suitable for the purposes herein as long as at least one undesired substance, as defined herein, is contained therein.

Whenever reference to blood is made in the context of the first chamber, or of the dialysis unit, or of the dialyzer, or in any other extracorporeal context, this need not necessarily mean pure blood, as taken from the human or animal body. In some embodiments, the term blood can refer to a mixture of blood, as taken from the human or animal body, and an acceptable additive in an acceptable amount. An additive is acceptable if the function of the blood is not significantly negatively affected. The amount of the additive is acceptable, if addition of the additive does not result in a significant volume increase of the blood, as taken from the human or animal body, so that the volume of the blood increases by not more than 50%, preferably not more than 40%, not more than 30%, not more than 20%, not more than 10%, not more than 5%.

In some embodiments, the systems and methods described herein are applied exclusively to in vitro activities. In alternative embodiments, the systems and methods described herein are exploited to address medical needs of a living subject, as described in detail below. In these alternative embodiments, the contacting of blood across a semipermeable membrane with a dialysis liquid also occurs in vitro, (i.e. outside the body of a human or animal), or extracorporeal. Additionally, interaction with the human or animal body occurs, as described below.

A suitable blood flow rate is up to 600 ml/min, or in case of two parallel devices up to 1200 ml/min, but usually much lower.

Undesired Substances in the Blood and Removal of the Same

In the broadest sense, the at least one undesired substance to be removed is a substance resulting from metabolic activity. Preferably, the at least one undesired substance is one or more of carbon dioxide ($CO_2$), hydrogen cation ($H^+$), hydrogen carbonate ($HCO_3^-$), carbonic acid ($H_2CO_3$), and solvates of any one thereof, and any combinations of these. It is known that in aqueous environments (e.g. aqueous solution or aqueous suspension, such as e.g. blood or dialysis liquid), these undesired substances relate to each other as expressed by the following equilibrium equation:

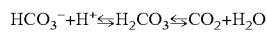

$$HCO_3^- + H^+ \leftrightharpoons H_2CO_3 \leftrightharpoons CO_2 + H_2O$$

The reactants (educts and products) of this reaction are present in dynamic equilibrium, as qualitatively indicated by the arrows (±) in the above equation. The dissociation of carbonic acid ($H_2CO_3 \leftrightharpoons CO_2 + H_2O$) is typically catalyzed or aided by the enzyme carboanhydrase which is present in erythrocytes. In accordance with the general principles of a dynamic equilibrium, the removal of one reactant causes, by Le Chatelier's principle, a shift of the reaction. $ECCO_2R$ systems of the prior art rely on the use of a gas exchange membrane, across which one reactant, carbon dioxide, diffuses out of the extracorporeal blood into a gas chamber. In contrast, the present invention enables the removal of at least one undesired substance from one liquid (blood) directly into another liquid (dialysis liquid). Therefore, the systems and methods described herein are not limited to the removal of gaseous undesired substances (such as $CO_2$), and do not require the transfer of undesired substances into the gas phase. It is thus contemplated that carbon dioxide is not transferred into the gas phase in the systems and methods described herein.

In general, one of the forms in which $CO_2$ is transported in the blood is in the form of carbamino groups, wherein carbon dioxide is attached to the terminal amine groups of proteins in the blood, primarily hemoglobin (then termed carbaminohemoglobin). In general, it is understood that the formation of carbamino groups is rapid and reversible and does not require catalysis by any enzyme. Thus, carbon dioxide in the carbamino form is also rapidly released from the amino group of blood proteins such as hemoglobin when the carbon dioxide concentration decreases in its surrounding as a result of diffusion into the dialysis liquid, so that, in accordance with Le Chatelier's principle, a new equilibrium is established. As described above, carbaminohemoglobin and dissolved carbon dioxide are also in equilibrium with the bicarbonate ($HCO_3^-$)/$H^+$-ion pair, but rapid conversion via $H_2CO_3$ requires the enzyme carbonic anhydrase. Carbonic anhydrase is naturally present in erythrocytes.

Therefore, in systems and methods described herein, all three major forms of carbonate present in blood, (i) protein (hemoglobin)-bound $CO_2$ in the form of carbaminohemoglobin, (ii) free $CO_2$, and (iii) bicarbonate ($HCO_3^-$)/$H^+$, can be removed, directly or indirectly, across the semipermeable membrane. While free $CO_2$ and bicarbonate ions can cross the semipermeable membrane along the concentration gradient into the dialysis liquid, hemoglobin-bound $CO_2$ becomes preferentially released from hemoglobin when e.g. the concentration of free $CO_2$ decreases as a result of diffusion into the dialysis liquid, so that, in accordance with Le Chatelier's principle, a new equilibrium between the three major forms of carbonate present in blood (transportation forms) is established. Importantly, in the systems and methods described herein the different transportation forms of carbon dioxide do not have to be transferred to the gas phase to be removed. Thus, blood-gas contact is not required, and preferably not foreseen. The systems and methods described herein enable removing all major transportation forms of carbon dioxide from the blood completely in a liquid medium. Depending on the bicarbonate ($HCO_3^-$) concentration of the dialysis liquid and of the blood, bicarbonate can be removed from the blood along the concentration gradient between the dialysis liquid on the one side and blood on the other side of the semipermeable membrane.

In the context of the systems and methods described herein, these undesired substances can be removed directly by transfer into the dialysis liquid along the concentration gradient (direct removal). Alternatively or additionally, the undesired substances can be removed indirectly by reaction with substances transferred from the dialysis liquid into the blood, which also results in a net removal of the undesired substance from the blood (indirect removal): for example, hydrogen cations can be indirectly removed from the blood by transferring $OH^-$ ions from the dialysis liquid into the blood, which is achieved because the pH of the dialysis liquid used in the present invention is typically more alkaline than the pH of the blood to be treated. Also other undesired substances, such as carbonic acid, carbonate, hydrogen carbonate, can be removed indirectly by transferring substances from the dialysis liquid into the blood, and their influence on the bicarbonate equilibrium.

In contrast to prior art systems that remove carbon dioxide in the gas phase, the systems and methods described herein enable removing substances that are soluble in liquids. These substances include ions of any type, as long as they are soluble in water, and hydrogen cations and bicarbonate anions in particular. The systems and methods described herein therefore allow for more complete, and thus more efficient, removal of metabolites from the blood than the $ECCO_2R$ methods of the state of the art. The mechanism of carbon dioxide removal according to the systems and methods described herein allow that the dissolved gas diffuses from one liquid phase to another liquid phase.

A dialysis unit comprising two chambers, as described in detail below, can suitably be used in the systems and methods described herein. The first chamber is suitable for receiving the blood. The first chamber suitably has an inlet (for entering blood) and an outlet (for exiting blood).

It is desired that the blood, when a dialysis unit is used in the systems and methods described herein, exits the first chamber (outlet) when its pH lies in the range of pH 7.35 to 7.45, preferably 7.36 to 7.44, more preferably 7.37 to 7.43, more preferably 7.38 to 7.42, more preferably 7.39 to 7.41, and most preferably about 7.40. Preferably, the blood is returned into the human or animal body after exiting the first chamber (outlet). Suitable tubing and connections are known in the art and can be employed in the context of the systems and methods described herein.

Optionally, it is foreseen to remove bubbles (if any), from the blood, i.e. at a stage after exit from the first chamber (outlet), and prior to reintroduction of the blood into the human or animal body. For this purpose, one or at least one bubble trap can be placed behind the first chamber. This is particularly suitable if blood is also exposed to a gas or to a gas-saturated or gas-supersaturated liquid, during at least part of the process.

Dialysis Fluid

The dialysis liquid of the systems and methods described herein is an aqueous liquid, i.e. a liquid comprising water.

The dialysis liquid suitable for the systems and methods described herein is characterized as follows:
(i) it has a pH the range from pH 8.0 to pH 11.0; and
(ii) it comprises at least one buffering agent, wherein the buffering agent is characterized by at least one pKa value in the range from 7.0 to 11.0;
(iii) it has a buffering capacity for $H^+$ ions which is 12 mmol/l $H^+$ ions or more.

These conditions concerning buffering agent, buffering capacity and pH are also referred to as "framework conditions" herein. Within the framework, more specific conditions may be appropriately selected, as described below.

A buffering capacity for $H^+$ ions which is 12 mmol/l $H^+$ ions or more is typically a buffering capacity which exceeds the buffering of blood plasma (pH 7.45; see Example 1). Thus, in the systems and methods described herein, the buffering capacity of the dialysis liquid typically exceeds the buffering of blood plasma (pH 7.45). In other words, the buffering capacity of the dialysis liquid is typically a buffering capacity for 12 mmol/l or more $H^+$ ions.

In general, according to the systems and methods described herein, the dialysis liquid features at least one buffering agent(s), typically at least two buffering agents. The use of a buffered dialysis liquid in general, and of the specific dialysis liquid of the systems and methods described herein in particular, allows performing the carbon dioxide removal in a pH range which is not detrimental to blood, while the actual capacity of the dialysis liquid for ions is much higher than it would be if the buffering agent(s) were not contained. The at least one buffering agent(s) provides, or contributes to, the buffer capacity of the dialysis liquid. It was surprising to find that the use of a dialysis liquid (as opposed to a sweep gas as in conventional $CO_2$ removal systems) is suitable for maintaining the pH of the dialysis liquid at acceptable pH levels.

Buffering Capacity for $H^+$ Ions

In the context of the systems and methods described herein, the term "buffering capacity for $H^+$ ions" or simply "buffering capacity" is an abstract value expressing the capacity of a given liquid to buffer the addition of $H^+$ ions. The term "buffering capacity for $H^+$ ions" is an inherent property of a respective liquid (aqueous solution). Also blood plasma is such a liquid. The determination of buffering capacity of blood plasma requires a step of centrifugation; the centrifugation results in pelleting of blood cells including platelets, and the supernatant is termed plasma. Such centrifugation is described in example 1. Suitable conditions for centrifugation of blood, and thus for the preparation of blood plasma are known in the art.

Precisely, the term "buffering capacity for $H^+$ ions" refers to the capacity to buffer a certain amount of $H^+$ ions, without reaching a pH lower than 6.5. "Without reaching a pH lower than 6.5" means that the pH of a properly mixed liquid does not reach a value of lower than pH 6.5. Thus, adequate mixing is important in practical assessment of the buffering capacity. Thus, as used herein, in the context of the dialysis liquid of the systems and methods described herein, the term "buffering capacity for $H^+$ ions" can be used solely for liquids having a pH of 6.5 or more. As defined herein, a solution having a pH of 6.5 would have a buffering capacity for $H^+$ ions of zero mmol/l (0 mmol/l). The dialysis liquids of the systems and methods described herein all have a pH much higher than 6.5, i.e. as defined herein; and therefore, they do have a buffering capacity for $H^+$ ions. If the buffering capacity is 12 mmol/l $H^+$ ions or more, the respective liquid (dialysis liquid) has a buffering capacity for $H^+$ ions according to the systems and methods described herein. More preferred are buffering capacities higher than that, i.e. buffering capacities for $H^+$ ions of 12 mmol/l or more, 14 mmol/l or more, 16 mmol/l or more, 18 mmol/l or more, 20 mmol/l or more, 22 mmol/l or more, 24 mmol/l or more, 26 mmol/l or more, 28 mmol/l or more, 30 mmol/l or more, 32 mmol/l or more, 34 mmol/l or more, 36 mmol/l or more, 38 mmol/l or more, 40 mmol/l or more, 42 mmol/l or more, 44 mmol/l or more, 46 mmol/l or more, 48 mmol/l or more, 50 mmol/l or more. Thus, the dialysis liquid according to the systems and methods described herein typically has a buffering capacity for $H^+$ ions of 12 or more mmol/l, such as more than 12 mmol/l. Preferred buffering capacities lie in the range from 12 to 50 mmol/l, more than 12 to 40 mmol/, 13 to 30 mmol/l, 14 to 25 mmol/l, 15 to 24 mmol/l, 16 to 23 mmol/l, 17 to 22 mmol/l, 18 to 21 mmol/l, 19 to 20 mmol/l.

The buffering capacity is not solely dependent on the pH of the respective liquid, but influenced by the composition of the liquid (presence and concentration of buffering compounds in the said liquid). Buffering capacity for $H^+$ ions is indicated as a number value, with the unit "mmol/l". According to the present invention, the buffering capacity for $H^+$ ions (buffering capacity in mmol/l) is determined by the following four-step assay:

1. The assay is suitable for determining the buffering capacity for $H^+$ ions of a given liquid (dialysis liquid or candidate dialysis liquid) that has a pH in the pH range of the dialysis liquids of the systems and methods described herein, i.e. pH 8.0 to pH 11.0, or subrange thereof. Thus, in a first step, it is tested whether the given liquid has a pH within that range. If that is not the case, the given liquid is not a dialysis liquid according to the present invention (no further testing necessary). If that is, however, the case, then the buffering capacity of the given liquid is determined by means of the following steps 2 and 3:

2. The liquid is subjected to titration with HCl. In particular, 0.1 M HCl is added, the solutions are agitated to ensure mixing, the pH is continuously monitored, and titration is terminated exactly when the pH of the liquid subject to titration reaches a final value of pH 6.5. In other words, titration is stopped when the pH reaches a value of 6.5. Based on the amount of HCl added until pH 6.5 is reached, the buffering capacity ($H^+$-ion in mmol/l) is calculated. This is possible because HCl is a strong acid which, according to the common general knowledge, dissolves completely in aqueous solution. Thus, 0.1 M HCl (0.1 mol/l) contains 0.1 mol/l dissolved ions and 0.1 mol/l dissolved $H^+$ ions. Based on the volume of HCl required for a given liquid to reach a pH of 6.5 upon titration, the amount of $H^+$ ions can be calculated that is buffered by said volume of dialysis liquid. If the amount of the given liquid used in the assay is 1 liter, the amount of $H^+$ ions that is buffered by 1 l dialysis liquid (buffering capacity in mmol/l) is directly obtained. If the amount of the given liquid used in the assay is a defined amount which is more than 1 liter or less than 1 liter, the amount of $H^+$ ions that can be buffered by 1 l dialysis liquid (buffering capacity in mmol/l)) is obtainable by simple mathematical calculation.

3. The buffering capacity as determined in step 2 (mmol/l) is compared to a reference value. Suitable reference values are 10 mmol/l; 11 mmol/l, 12 mmol/l, 13 mmol/l, 14, mmol/l; whereby 12 mmmol/l is strongly preferred. Alternatively, the reference value is represented by the buffering capacity of human or animal (pork, mouse) blood; in that case, the buffering capacity of blood plasma is determined as described in above step 2.

4. If the buffering capacity of the given solution (mmol/l) exceeds the reference value (mmol/l), the given solution is determined to have a buffering capacity according to the systems and methods described herein.

In the assay for determining buffering capacity, all pH measurements, as well as the titration, is performed at room temperature (temperature of all solutions and equipment; surrounding temperature). The above assay is straightforward and can be performed by one of ordinary skill in the art with minimal effort, based on the guidance herein and on the common general knowledge. Thereby, the buffering capacity of a given liquid can be readily and reliably determined without undue burden.

An example of determination of buffering capacity, as defined in the systems and methods described herein, is given below in Example 1. As shown by this example, blood plasma having pH 7.45 typically has a buffering capacity of 12 mmol/l. However, it is conceivable that blood plasma from other sources (other species and/or other individuals) has a different buffering capacity. Other conceivable blood plasma buffering capacities lie in the range of 3 to 30 mmol/l, preferably 4 to 25 mmol/l, preferably 5 to 20 mmol/l, preferably 6 to 19 mmol/l, preferably 7 to 18 mmol/l, preferably 8 to 17 mmol/l, preferably 9 to 16 mmol/l, preferably 10 to 15 mmol/l, preferably 11 to 14 mmol/l, preferably 12 to 13 mmol/l.

It is preferable that the dialysis liquid according to the systems and methods described herein typically has a buffering capacity which exceeds the buffering capacity of blood plasma. When blood of an individual, e.g. a patient, is treated in the process or method of the present invention, then the buffering capacity for $H^+$ ions is preferably selected such that it exceeds the buffering capacity of blood of that individual, e.g. that patient.

pH of the Dialysis Fluid

Preferred pH ranges of the dialysis liquid include pH 8.0 to pH 11, pH 8.0 to pH 10.0, pH 8.0 to pH 9.5, and preferably pH 8.0 to pH 9.0. Thus, the at least one pKa value of the at least one buffering agent present in the dialysis liquid is in the range from pH 7.0 to pH 11.0; pH 8.0 to 10.5, 8.0 to 10.0, 8.0 to 9.5, and preferably 8.0 to 9.0. If more than one buffering agent is present, it is preferably that each of them has a pKa value in the above range or subrange. If the at least one buffering agent has more than one pKa value, at least one said pKa value, preferably more than one said pKa values, lie(s) is in the above range or subrange. Any buffering agent having at least one pKa value in the range from 7.0 to 11.0 is theoretically suitable for buffering in the desired pH range. However, in the context of the systems and methods described herein, the buffering agent must be selected such that it is not toxic or does not cause undesired side effects in the human or animal being that is subject to dialysis. Particularly suitable buffering agents are the carbonate/bicarbonate system, Tris, and water-soluble proteins (preferably albumin), all as defined above. Another suitable pH value of the dialysis liquid is the range from pH 7.75 to pH 9.0. In general, preferred pH values lie in the range from pH 7.75 to pH 9.0, preferably from pH 8.0 to pH 9.0, preferably from pH 8.1 to pH 8.9, preferably from pH 8.2 to pH 8.8, preferably from pH 8.3 to pH 8.7, more preferably from pH 8.4 to pH 8.6, and most preferably at or around pH 8.5. It is important to note that these are general preferred ranges and subranges. For specific purposes, such as for treating blood from a specific patient subgroup, alternative, different or partially diverging ranges may be preferable, as described below. The pH can be adjusted by the amount or concentration of buffering substances, such as bicarbonate and hemoglobin, within the ranges contemplated herein, and/or adjusted by addition of an acid or base, such as hydrochloric acid or sodium hydroxide.

Bicarbonate and hydrogen cations, as well as other small molecules, including ions or substances which can influence the pH of an aqueous liquid, can traverse the semipermeable membrane during the process of the present invention. Therefore, the pH of the dialysis liquid does not necessarily remain constant throughout the process step of contacting blood with the dialysis liquid. Therefore, in a precise sense, the pH of the dialysis liquid, as defined herein, is preferably defined for the dialysis liquid at the stage immediately preceding the contacting of blood, e.g. at the stage wherein the dialysis liquid enters the second chamber of a dialysis unit as described herein.

Buffering Agent in the Dialysis Fluid

Suitable buffering agents present in the dialysis liquid include in particular any one or more of the following: Tris(hydroxymethyl)aminomethane (Tris, THAM); carbonate/bicarbonate; water-soluble proteins, preferably albumin.

Bicarbonate is characterized by an acidity (pKa) of 10.3 (conjugate base carbonate). Thus, in an aqueous solution containing bicarbonate, carbonate may be present as well, depending on the pH of the solution. For matters of convenience, the expression "carbonate/bicarbonate" is used herein to refer to both bicarbonate and its corresponding base carbonate. "carbonate/bicarbonate concentration" or "(combined) carbonate/bicarbonate concentration", or the like, refers herein to the total concentration of carbonate and bicarbonate. For example, "20 mM carbonate/bicarbonate" refers to a composition having a 20 mM total concentration of bicarbonate and its corresponding base carbonate. The ratio of bicarbonate to carbonate will typically be dictated by the pH of the composition.

Bicarbonate and hydrogen cations, as well as other small molecules, including ions or substances which can influence the pH of an aqueous liquid, can traverse the semipermeable membrane during the process of the present invention. Therefore, in a precise sense, the (combined) carbonate/bicarbonate concentration of the dialysis liquid, as defined herein, is preferably defined for the dialysis liquid at the stage immediately preceding the contacting of blood, e.g. at the stage wherein the dialysis liquid enters the second chamber of a dialysis unit as described herein.

Tris(hydroxymethyl)aminomethane, usually called "Tris". Tris(hydroxymethyl)aminomethane is also known as "THAM". Tris is an organic compound with the formula $(HOCH_2)_3CNH_2$. The acidity (pKa) of Tris is 8.07. Tris is non-toxic and has previously been used to treat acidosis in vivo (e.g. Kallet et al., *Am. J. of Resp. and Crit. Care Med.* 161: 1149-1153; Hoste et al., *J. Nephrol.* 18: 303-7.). In an aqueous solution comprising Tris, the corresponding base may be present as well, depending on the pH of the solution. For matters of convenience, the expression "Tris" is used herein to refer to both Tris(hydroxymethyl)aminomethane and its corresponding base, unless the context dictates otherwise. For example, "20 mM Tris" refers to a composition having a 20 mM total concentration of Tris and its corresponding base. The ratio of Tris(hydroxymethyl)aminomethane to its corresponding base will be dictated by the pH of the composition. Tris and its conjugate base, as well as other small molecules, including ions or substances which can influence the pH of an aqueous liquid, can traverse the semipermeable membrane during the methods described herein. Therefore, in a precise sense, the Tris concentration of the dialysis liquid, as defined herein, is preferably defined for the dialysis liquid at the stage immediately preceding the contacting of blood, e.g. at the stage wherein the dialysis liquid enters the second chamber of a dialysis unit as described herein.

A water-soluble protein is suitable for the purposes of the systems and methods described herein if it has at least one imidazole (histidine side) chain and/or at least one amino group (lysine) side chain or at least one sulfhydryl (cysteine) side chain. These side chains typically have pKa values in the range from 7.0 to 11.0. A protein falls under the definition water-soluble if at least 10 g/l of the protein is soluble in aqueous solution having a pH within the range of the dialysis liquid of the present invention, e.g. pH 8.0. A strongly preferred water-soluble protein in the context of the present invention is albumin, as defined in the following.

Albumin is a preferred water-soluble protein in the context of the systems and methods described herein. In general, albumin has good buffering capacity in the desired pH range, typically, owing to several amino acid side chains with respective pKa values. In the systems and methods described herein, albumin is preferably serum albumin of a human or animal, such as human serum albumin, animal albumin (e.g. bovine serum albumin), or alternatively genetically engineered albumin, or mixtures of any one or more of these. Mixtures containing albumin and at least one further carrier substance are also possible. In any case, the albumin concentration specified herein refers to the total concentration of albumin, no matter if one single type of albumin (e.g. human serum albumin) or a mixture of various types of albumin is being employed. The dialysis liquid used in the systems and methods described herein features 10 to 60 g/l albumin, preferably 15 to 30 g/l albumin, preferably 20 to 25 g/l albumin, and most preferably 30 or about 30 g/l albumin. The concentration of albumin can also be indicated as % value; i.e. 20 g/l albumin corresponds to 2% albumin (wt./vol). Albumin is a second buffering agent in the dialysis liquid according to the present invention. The albumin in the dialysis liquid contributes to its buffering capacity, and binds carbonate in the form of carbamino groups. The pH range in which albumin can suitably buffer liquids, such as blood, is well known in the art, e.g. from biochemistry textbooks. The presence of albumin in the dialysis liquid facilitates the removal of protein-bound substances from blood. In view of its property to adsorb or bind compounds such as hydrogen cations, carbon dioxide and toxins, albumin can also be more generally referred to as an adsorber, or adsorber molecule.

In addition to albumin's suitability for binding an undesired substance of the type described above, and thus its suitability in methods for extracorporeal carbon dioxide removal and of blood pH adjustment, the presence of albumin in the dialysis liquid, as in the systems and methods described herein, further enables or enhances the removal of the protein-bound toxins. For this purpose it is possible to exploit a capacity of the albumin present in the dialysis liquid: in general, albumin is known to bind to the unbound toxins, and this property can be taken advantage of when albumin is present in the dialysis liquid, thus enabling the binding of toxins traversing the semipermeable membrane from blood into the dialysis liquid. This method is called "albumin dialysis" (see e.g. WO 2009/071103 A1, incorporated herein by reference in its entirety).

A suitable total concentration of carbonate/bicarbonate (combined concentration of both substances together) is 0 to 40 mmol/l. The presence of carbonate/bicarbonate in the dialysis liquid contributes to buffering capacity of the dialysis liquid. However, the lower the concentration of carbonate/bicarbonate, the better the removal of $CO_2$ from the blood. Therefore, it may be preferable to use a dialysis liquid devoid of carbonate/bicarbonate, or without addition of carbonate/bicarbonate. The pH range in which bicarbonate can suitably buffer liquids, such as blood is well known in the art, e.g. from biochemistry textbooks. When the dialysis liquid of the systems and methods described herein is prepared, bicarbonate can be added in the form of any of its salts, such as sodium bicarbonate, potassium bicarbonate, and others, or alternatively be added indirectly by introducing carbon dioxide, optionally in the presence of carbonic anhydrase, and adjusting the pH as required by addition of a suitable base, such as sodium hydroxide or potassium hydroxide, sodium hydroxide being strongly preferred. In case of addition in the form of a salt, sodium bicarbonate or sodium carbonate is strongly preferred. Alternatively, potassium salts, or mixtures of sodium and potassium salts, can be used. Salts particularly useful to be added to dialysis liquid at high pH (e.g. up to pH 11) are sodium carbonate or potassium carbonate. In general, preferred (combined) carbonate/bicarbonate concentrations in the dialysis liquid, with reference to the stage of entering the second chamber in the process of the systems and methods described herein, lie in the range from 10 to 40 mmol/l, preferably 15 to 35 mmol/l, more preferably 20 to 30 mmol/l, and most preferably at or about 30 mmol/l. It is important to note that these are general preferred ranges and subranges. For specific purposes, such as for treating blood from a specific patient subgroup, alternative, different or partially diverging ranges may be preferable, as described below. Alternative suitable (combined) carbonate/bicarbonate concentrations lie in the range from 0 to 40 mmol/l, or more than 0 to 40 mmol/l, preferably 5 to 35 mmol/l, preferably 10 to 30 mmol/l, more preferably 15 to 25 mmol/l, and most preferably at or about 25 mmol/l. When the dialysis liquid is recycled, the (combined) carbonate/bicarbonate concentration is determined, and adjusted if required, prior to entering of the dialysis liquid into the second chamber. In general, (combined) carbonate/bicarbonate concentrations above 40 mmol/l are not desired in view of possible side effects.

Suitable Tris concentrations are in the range from 0 to 40 mmol/l, or more than 0 to 30 mmol/l, preferably 5 to 25 mmol/l, preferably 10 to 20 mmol/l, more preferably about 15 mmol/l. Alternative suitable Tris concentrations are in the range from 0-38 mmol/l, or 0-20 mmol/l.

A suitable concentration of albumin is 10 to 60 g/l (i.e. 1 to 6 g/100 ml). In this specification, g/l, and g/100 ml, refers to the grams per volume (final volume of the albumin-containing liquid). Preferably, albumin is not the only buffering agent present in the dialysis liquid. Thus, preferably, either carbonate/bicarbonate or Tris is present in addition to albumin. A preferred dialysis liquid according to the systems and methods described herein features both (i) carbonate/bicarbonate and (ii) albumin; or both (i) Tris and (ii) albumin. Particularly, when no carbonate/bicarbonate is added to the dialysis liquid (i.e. the carbonate/bicarbonate concentration in the dialysis liquid is 0 mmol/l or near 0 mmol/l), then it is preferable that both Tris and albumin are present in the dialysis liquid. Alternatively, Tris is the only buffering agent comprised in the dialysis liquid.

All the above ranges and concentrations of Tris, carbonate/bicarbonate and albumin are combinable in the systems and methods described herein.

Further Properties of the Dialysis Fluid

The dialysis fluid typically comprises water. Typically more than 50% (vol./vol.), more than more than 60% (vol./vol.), more than 70% (vol./vol.), more than 80% (vol./vol.), or more than 90% (vol./vol.), of the dialysis liquid is water. Other water-miscible liquids can also be comprised in the dialysis liquid.

The systems and methods described herein not only provide a process for removing an undesired substance, but also a dialysis liquid as such, which is suitable for said purpose. Any and all specific dialysis liquid described herein is a subject of the present invention.

Preferably, albumin is not the only buffering agent present in the dialysis liquid. Thus, preferably, either carbonate/bicarbonate or Tris is present in addition to albumin. A preferred dialysis liquid according to the systems and methods described herein features both (i) carbonate/bicarbonate and (ii) albumin; or both (i) Tris and (ii) albumin. An alternative preferred dialysis liquid comprises Tris as the only buffering agent, i.e. does not contain added carbonate/bicarbonate or albumin. In general, carbonate/bicarbonate, albumin and Tris are buffering agents, and thus can all contribute to maintenance of the pH within a desired range. These buffering agents have at least one pKa value in the pH range defined above.

It is not necessary to maintain the dialysis liquid at the pH desired upon beginning of exposure to blood (entry into the second chamber) at all times. Particularly when the dialysis liquid is being recycled, as described below, pH and (combined) carbonate/bicarbonate concentration may vary over time. However, at the stage of entering into the second chamber, the dialysis liquid is adjusted to comply with the specified pH and bicarbonate/albumin concentrations. For example, the pH can be measured by at least one pH measuring device before the dialysis liquid enters the second chamber. Optionally, the pH can additionally be measured by at least one pH measuring device A first particular dialysis liquid useful in the present invention features 0 to 40 mmol/l carbonate/bicarbonate (preferably 10 to 40 mmol/l carbonate/bicarbonate), 10 to 60 g/l albumin (i.e. 1 to 6 g/100 ml albumin), and has a pH the range from pH 7.75 to pH 11.0, preferably pH 8.0 to pH 10.0, and more preferably pH 8.0 to pH 9.0. Preferred carbonate/bicarbonate concentrations are as specified above.

A second particular dialysis liquid useful in the systems and methods described herein features 0 to 40 mmol/l Tris (preferably 1 to 20 mmol/l Tris), 10 to 60 g/l albumin (i.e. 1 to 6 g/100 ml albumin), and has a pH the range from pH 7.75 to pH 11.0, preferably pH 8.0 to pH 10.0, and more preferably pH 8.0 to pH 9.0. Preferred Tris concentrations are as specified above.

A third particular dialysis liquid useful in the systems and methods described herein features 0 to 40 mmol/l Tris (preferably 1 to 20 mmol/l Tris). Preferred Tris concentrations are as specified above. A suitable buffering capacity is generally provided for Tris-buffered dialysis liquids when the pH is relatively high. Thus, in the case of absence of additional buffering agents, such as carbonate/bicarbonate and albumin, the pH of the dialysis liquid is suitably particularly high, e.g. 8.5 to 11.0, or 9.0 to 10.5, preferably 9.0 to 10.0.

The dialysis liquid can also feature other membrane-permeable small molecules for transfer into blood, if desired, e.g. glucose. Preferably, the dialysis liquid features calcium ($Ca^{2+}$) ions. In contrast to prior art dialysis liquid, which contains only free calcium ions, the dialysis liquid of the systems and methods described herein is typically characterized in that the calcium ions are at least partially bound to albumin. In general, at higher pH values, more calcium is bound to albumin, and less is available for exchange with the blood. Therefore the total calcium in the albumin-containing dialysis liquid according to the systems and methods described herein contains higher calcium concentrations that known from dialysis liquids according to the state of the art. In particular, the calcium ion concentration of albumin-containing dialysis liquid is 1.7 mmol/l or higher. This is desired in order to have enough free calcium available, i.e. to not decrease the free calcium ion concentration in the blood (see Example 3).

Preferably the dialysis liquid features 2 to 4 mmol/l calcium ($Ca^{2+}$) ions, more preferably 2.4-2.6 mmol/l calcium ions. Calcium ions can be added in the form of any suitable salt, e.g. calcium chloride. Addition of calcium into the dialysis liquid is beneficial because blood also contains calcium. The presence of calcium in the dialysis liquid prevents undesired net flux (leaking) of calcium ions from the blood into the dialysis liquid. Although it is known that calcium ions can precipitate at very basis pH, the presence of calcium is not incompatible with the systems and methods described herein in view of the maximum pH value of 9.0 of the dialysis liquid at the stage of being brought into contact with blood across the semipermeable membrane. In case the dialysis liquid has a pH higher than 10, some ions such as calcium ions (and others) are insoluble. Therefore, if the dialysis liquid has a pH of higher than 9, it is preferable that no calcium ions (and other insoluble ions) are present. In order not to deplete a patient of such ions, they should be infused directly into the blood of the patient, if the dialysis liquid has a pH in that range.

Preferably, the dialysis liquid has an osmolarity that is substantially identical to the osmolarity of blood being dialyzed.

In addition to the above, the enzyme carbonic anhydrase may be added to the dialysis liquid, or may be present in the dialysis liquid. Carbonic anhydrases are enzymes which promote the reversible reaction from carbon dioxide to bicarbonate ($HCO_3^-$) and $H^+$-ions. Carbonic anhydrases can be added to the extracorporeal blood circuit. It is also possible to coat the inside surface of the first or second chamber with carbonic anhydrases. In general, and in addition to the aspects described above, a dialysis liquid suitable for the physiological purposes of the systems and methods described herein preferably contains the desired electrolytes, nutrients and buffers in adequate concentrations, so that their levels in the patient's blood can be adjusted, e.g. brought to normal physiological values, or to any otherwise desired or indicated values. Optional constituents of the dialysis liquid according to the systems and methods described herein include electrolytes, preferably selected from sugars and/or salts (anions/cations/zwitterions). Typical cations include calcium, magnesium, potassium and sodium ions; typical anions include chloride, $HCO_3^-$, $H_2CO_3$, $HPO_4^{2-}$, $H_2PO_4^-$; typical zwitterions include amino acids (e.g. histidine) and peptides or salts of fruit acids.

Preferably, the dialysis liquid contains no added acetic acid and no added acetate. Preferably, the combined concentration of acetic acid in the dialysis liquid is less than 4 mmol/l, less than 3 mmol/l, less than 2 mmol/l, less than 1 mmol/l, most preferably 0 mmol/l.

Adaptation of the Dialysis Fluid to the Methods

In view of the general versatility of the dialysis liquid employed in the systems and methods described herein, i.e. the suitability for adjusting the blood pH as well as the suitability for removing carbon dioxide, directly or indirectly, from the blood, as well as combinations thereof, the dialysis liquid can be designed to specifically or primarily address a particular goal. For example, the dialysis liquid may be designed to the goal of adjusting the blood pH, or to the goal of removing carbon dioxide—directly or indirectly. In this context, the terms design and adaptation of the dialysis liquid are used interchangeably and refer to the dialysis liquid immediately prior to exposure to blood via the semipermeable membrane, i.e. at the stage of entering the second chamber.

For example, when blood from a subject suffering from metabolic acidosis is to be subjected to the process of the present invention, then it will typically be desired to adjust the pH, while removal of carbon dioxide may not be desired, or not indicated. By removing preferably $H^+$ ions, $CO_2$ serves as a source for production of bicarbonate. In another example, when blood from a subject suffering from respiratory acidosis is to be subjected to the systems and methods described herein, then it will typically be desired to adjust the pH and to remove carbon dioxide. The dialysis liquid used in the systems and methods described herein can be adapted to such purposes, within the general framework of the dialysis liquid as described herein.

Depending on the bicarbonate ($HCO_3^-$) concentration of the dialysis liquid and of the blood, bicarbonate can be removed from the blood along the concentration gradient between the dialysis liquid on the one side and blood on the other side of the semipermeable membrane. In other words, as long as the (combined) carbonate/bicarbonate concentration in the dialysis liquid is lower than the (combined) carbonate/bicarbonate concentration in the blood, bicarbonate will be removed from the blood into the dialysis liquid along the concentration gradient. If removal of bicarbonate from the blood is not desired or not indicated, the (combined) carbonate/bicarbonate concentration of the dialysis liquid is selected such that it is not lower than the (combined) carbonate/bicarbonate concentration of the blood. "not lower," in this context, means equal or higher, such as slightly higher, but typically means roughly equal or equal.

Generally, a dialysis liquid adjusted for treating blood from a subject suffering from metabolic acidosis comprises bicarbonate preferably in the concentration range from 16 to 40 mmol/l. Preferably, the concentration is increased slowly during the course of treatment, so as to avoid acidosis of the cells. Preferred embodiments of the (combined) carbonate/bicarbonate concentration for such purposes include the range from 25 to 35 mmol/l, or (about) 30 mmol/l.

On the other hand, generally, a dialysis liquid adjusted for treating blood from a subject suffering from respiratory acidosis comprises bicarbonate preferably in the concentration range from 0 to 40 mmol/l, or alternatively 5 to 40 mmol/l or 10 to 40 mmol/l. Preferred embodiments of the (combined) carbonate/bicarbonate concentration for such purposes include the range from 15 to 35 mmol/l, from 20 to 30 mmol/l, or (about) 25 mmol/l.

Suitability for pH Adjustment

Besides the efficient removal of metabolites, such as $CO_2$ and bicarbonate ions from the blood, the systems and methods described herein also allow for adjusting the pH of the blood to a desired level. This is suitable e.g. for the treatment of acidic blood, e.g. blood from acidosis patients. It is desired that the blood pH is adjusted to a predetermined value or a predetermined range within the range of pH 6.8 to pH 8.5. Blood pH values outside that range are not desired in view of undesired side effects, such as denaturation of blood proteins and/or precipitation of blood components. In general, adjusting the blood pH value or range means that the blood is characterized by said adjusted value or range at the stage of exit from the first chamber.

Given that physiological blood of a healthy human subject typically has a pH in the range of 7.35 to 7.45, i.e. around 7.40, it is in some embodiments desired to adjust the blood pH to a range or value encompassing that range, i.e. 7 to 8.5 7.0 to 7.8, 7.2 to 7.6, or 7.3 to 7.5. In preferred embodiments, when it is intended to bring the blood pH to a value near the value of physiological blood of a healthy human subject, it is desired to adjust the blood pH to a value or range within the range of pH 7.35 to 7.45, preferably 7.36 to 7.44, more preferably 7.37 to 7.43, more preferably 7.38 to 7.42, more preferably 7.39 to 7.41, and most preferably about 7.40.

As described in detail below, the systems and methods described herein are particularly suitable for treating subjects suffering from acidosis (acidosis patients), i.e. subjects suffering from metabolic and/or respiratory acidosis. In embodiments directed to, or suitable for, treating blood from acidosis patients, it may be desired to adjust the blood pH to a range or value that is more alkaline than 7.40, more than 7.40 to 8.0, 7.5 to 7.9, or 7.6 to 7.8, preferably within the range of pH 7.65 to 7.75, e.g. 7.7.

Adjustment of the blood pH in the systems and methods described herein is technically feasible because of the buffering capacity of the dialysis liquid used, and because of the permeability of the semipermeable membrane of $H^+$ and $OH^-$ ions. Thus, by using a buffered dialysis liquid, pH adjustment of the blood can be achieved. $H^+$ and $OH^-$ ions can cross the semipermeable membrane, and will do so across the respective concentration gradient.

Without being bound by any particular theory, it is understood that $H^+$-ions are eliminated from the blood mainly in view of the excellent buffering capacity of the dialysis liquid of the systems and methods described herein. In addition, it is thought that minor amounts of $H^+$ ions are removed by reacting with $OH^-$-ions, which are provided by the dialysis liquid, on either side or on both sides of the semipermeable membrane. The elimination of not only carbon dioxide from the blood, but also $H^+$-ions (by reaction with $OH^-$-ions) from the blood, enables adjusting the acid-base balance of the blood. As described in detail below, the dialysis liquid used in the systems and methods described herein can be adjusted based on the needs, e.g. based on the needs of a patient being subjected to treatment by dialysis. The systems and methods described herein thus allow for preferential removal of carbon dioxide, or for preferential adjustment of the blood pH, or both. This versatility is provided by the possibilities to adjust the pH of the dialysis liquid and to adjust the concentration of buffering substances (particularly albumin and bicarbonate) in the dialysis liquid, each independently from each other, within the general ranges as defined herein.

Suitability for Removal of a Toxin

In some embodiments, a further undesired substance, or additional undesired substance, can be removed from the blood. In respective embodiments, such a further undesired substance is a toxin, e.g. a protein-bound toxin. In such embodiments, it is intended to remove at least two undesired substances from the blood, e.g. at least one undesired substance as specified above, and additionally a toxin. The term toxin, as used herein, is not particularly limited and refers to any substance which is toxic to the human or animal body, including metabolites, e.g. bilirubin, bile acids; copper; other substances like hormones or drugs accumulating in hepatic failure. Typically, the toxin is protein-bound in the blood of the human or animal body. In general, protein-bound toxins are hardly removed by hemodialysis. The presence of albumin in the dialysis liquid, as in the systems and methods described herein, enables or enhances the removal of the protein-bound toxins: in the blood, a small proportion of the protein-binding toxins is in the free form in solution and this proportion can diffuse through the semipermeable membrane in the dialyser and bind to the free binding sites of the adsorber (albumin) in the dialysis liquid.

Semipermeable Membrane and Device Having the Same

A device suitable for the systems and methods described herein features a first chamber, suitable for receiving blood, and a second chamber, suitable for receiving the dialysis liquid. The first chamber and the second chamber are separated by at least one semipermeable membrane.

Suitably, the first chamber is divided into a multitude of first chambers. A multitude refers to any integer more than one. Thus, typically, multiple first chambers are present in the device. Preferably each first chamber is in contact with the second chamber across a semipermeable membrane. The first chambers are preferably present in the form of capillaries. This enables that the blood flows through the capillaries while being in contact with the dialysis liquid across the semipermeable membrane.

Optionally, multiple second chambers are present in the device. Preferably each second chamber is in contact with the first chamber across a semipermeable membrane.

In the device, the ratio of total volume of the (multitude of) second chambers to total volume of the (multitude of) first chambers can be in the range of 10:1 to 1:10. Preferably, the total volume of the (multitude of) second chambers is larger than the total volume of the (multitude of) first chambers. A preferred ratio is about 2:1.

Thus, in the systems and methods described herein, the transfer of the at least one undesired substance from the blood into the dialysis liquid occurs across a semipermeable membrane. The membrane is ideally permeable to oxygen, carbon dioxide, bicarbonate, $H^+$ ions and liquids. In a device featuring a first chamber for receiving blood and a second chamber for receiving dialysis liquid, the semipermeable membrane is present between the first chamber and the second chamber. This enables the transfer of membrane-permeable substances across from the first chamber into the second chamber or from the second chamber into the first chamber. Typically, such substances, as long as they are membrane permeable, will preferentially migrate along their concentration gradient.

The semipermeable membrane is not permeable for proteins of the size or properties of albumin. However, bicarbonate and hydrogen cations, as well as other small molecules, including ions or substances which can influence the pH of an aqueous liquid, can traverse the semipermeable membrane during the process of the present invention. Therefore, the pH of the dialysis liquid does not necessarily remain constant throughout the process step of contacting blood with the dialysis liquid. Therefore, in a precise sense, the pH and the (combined) carbonate/bicarbonate concentration of the dialysis liquid, as defined herein, are preferably defined for the dialysis liquid at the stage immediately preceding said contacting, i.e. the stage wherein the dialysis liquid enters the second chamber. In other words, the dialysis liquid, when entering the second chamber, has a pH the range from pH 8.0 to pH 11.0 (or any preferred value or subrange thereof, as defined in this specification).

While the transfer of substances across the semipermeable membrane is passive, i.e. along the concentration gradient, the blood/and/or the dialysis liquid are preferentially moved, e.g. by a constant flow of these liquids through the respective chamber, and optionally by stirring, shaking, pressure gradient (causing convection) or other suitable mechanical activity. Such mechanical activity is believed to contribute to efficient exposure of the substances to the surface of the semipermeable membrane, and thus to the efficiency of migration across the membrane.

Typically, in a device suitable for the systems and methods described herein, the exposed surface area of the semipermeable membrane can be in the range between 0.01 $m^2$ and 6 $m^2$. A (combined) surface area of up to 6 $m^2$ is typically present when two dialysis units are being used in parallel. Such parallel use of two dialysis units is contemplated in one embodiment of the systems and methods described herein. Typically, the exposed surface area of any one dialysis unit is in the range of between 0.01 $m^2$ and 3 $m^2$, such as between 0.1 $m^2$ and 2.2 $m^2$. In general, surface areas in the lower part of these ranges are particularly suitable for the treatment of children. Exposed surface area refers to the area of the semipermeable membrane exposed to the first chamber on the one side, and simultaneously exposed to the second chamber on the other side. Any additional sections of the membrane, which are not exposed to both chambers simultaneously, but e.g. fixed in a fixation means or otherwise not exposed, are not considered to be part of the exposed surface area. It is also possible that the systems and methods described herein use more than one such membrane, either in the same dialysis unit, or in more than one dialysis unit. If more than one dialysis unit is used, such more than one dialysis units can be present in a row, or in parallel, from the perspective of the extracorporeal blood stream. Preferably there are two devices for dialysis, each with an exposed surface area as disclosed above.

The systems and methods described herein thus allow for a transfer of carbon dioxide and other compounds, such as hydrogen cation and bicarbonate, to pass (through the dialysis membrane) into the dialysis liquid. Hence, the systems and methods described herein can be referred to as liquid/liquid dialysis systems and methods suitable for $CO_2$ removal. This allows for more efficient removal of metabolites, such as $CO_2$, from the blood than conventional methods.

While carbaminohemoglobin and dissolved carbon dioxide are in equilibrium with the bicarbonate ($HCO_3^-$)/$H^+$-ion pair, the rapid conversion requires the enzyme carbonic anhydrase. Optionally, the semipermeable membrane contains carbonic anhydrase activity. This can be achieved by coating the membrane, on the blood-facing side and/or on the side facing the dialysis liquid, with carbonic anhydrase.

Suitably, one chamber is provided on either side of the semipermeable membrane, i.e. a first chamber on one side of the semipermeable membrane, and a second chamber on the other side of the semipermeable membrane. In other words, a device is suitably used which features two compartments, divided by a semipermeable membrane. Preferably, the first chamber, the semipermeable membrane and the second chamber are present in one device. Thus, blood is present in the first chamber, and the dialysis liquid is present in the second chamber, the chambers being separated by said semipermeable membrane. It is also possible to coat the semipermeable membrane with the enzyme carbonic anhydrase.

Suitably, multiple first chambers are present, each in contact with the second chamber across a semipermeable membrane. Such multiple first chambers can have the form of capillaries; thus, in the process of that embodiment, blood streams through capillaries.

Although it is not impossible to employ the systems and methods described herein in a static system, i.e. where the blood is steadily present in the first chamber, i.e. without flowing (entering, passing through and exiting) that chamber and the dialysis liquid is steadily present in the second chamber, i.e. without flowing (entering, passing through and exiting) that chamber, semi-static and non-static embodiments are preferred. In non-static embodiments, blood flows through the first chamber, so that it enters, passes through and exits the first chamber, and the dialysis liquid flows through the second chamber, so that it enters, passes through and exits the second chamber. Embodiments in which only one of these liquids flows through its respective chamber, while the other one is steadily present in its respective other chamber, i.e. without flowing (entering, passing through and exiting) of the respective other liquid through that respective other chamber, are termed semi-static. Thus, preferably, in the systems and methods described herein, the blood flows through the first chamber and the dialysis liquid simultaneously flows through the second chamber. Thus, it is preferred that blood is passed through the blood compartment (first chamber) and that the dialysis liquid is passed through the dialysis liquid compartment (second chamber).

The systems and methods described herein make it possible to efficiently remove one or more undesired substance as defined above, including $CO_2$, without requiring a gas stream (sweep gas) as in the prior art. In particular, it is neither desired nor required to bring the undesired $CO_2$ into the gas phase. Typically, the dialysis unit used in the systems and methods described herein does not comprise a chamber having gas (sweep gas) in contact with blood across a membrane (e.g. gas exchange membrane).

Suitably, the device having the first chamber, second chamber and the semipermeable membrane is a dialysis unit, optionally present in a dialyzer. A dialysis unit is a unit featuring a first chamber as defined herein, a second chamber as defined herein, and a semipermeable membrane, as well as means for entering and removing a fluid (e.g. blood) into and from the first chamber (inlet and outlet), and means for entering and removing a fluid (e.g. dialysis liquid) into and from the second chamber (inlet and outlet). Thus, the first chamber features and inlet and an outlet, and the second chamber features an inlet and an outlet. Thus, in the systems and methods described herein, the dialysis unit features a biological fluid compartment (first chamber) that is part of the biological fluid circuit, a dialysis liquid compartment (second chamber) that is part of the dialysis liquid circuit, and a semipermeable membrane separating the biological fluid compartment and the dialysis liquid compartment. When a dialysis unit is used, the blood passes through the first chamber, and the dialysis liquid passes through the second chamber. Alternatively, the device is a device for ultrafiltration (ultrafiltration device). Preferably, during the methods described herein, the second chamber does substantially not comprise any gas phase, i.e. is filled substantially solely with dialysis liquid in the liquid phase. Thus, gas contact of the blood may be entirely excluded, or limited to a minimum, required under the circumstances, e.g. a bubble catcher or a similar device.

The semipermeable membrane used in the systems and methods described herein is not particularly limited, as long as it is permeable for water and inorganic molecules solubilized in water. A suitable semipermeable membrane allows for transfer of the at least one undesired substance across the semipermeable membrane. The membrane can e.g. be selected among conventional semipermeable membranes as currently used e.g. for hemodialysis. It is also conceivable, however, to consider membranes with larger pores than those presently used for dialysis. The diffusion through the membrane can optionally be supported by convective transport by means of filtration.

A dialyzer has a dialysis unit as described, and additionally tubing (inlet and outlet) connected with the respective means for entering and removing a fluid into and from said first and second chamber, respectively: the tubing connected to the first chamber (inlet and outlet) is suitable to be connected to the blood system of a human or animal. The dialyzer essentially comprises two chambers separated by a dialysis membrane, to each of which is connected a tubing system for the fluids to be used. Optionally, the tubing connected to the second chamber (inlet and outlet) is suitable to be connected to a regeneration unit. The latter setting allows for regeneration (recirculation, recycling) of the dialysis liquid, as described herein below, as well as in WO 03/094998 A1 and WO 2009/071103 A1, both incorporated herein by reference in their entireties. The dialyzers used in the systems and methods described herein are not particularly limited, and can be conventional dialysers currently used e.g. for haemodialysis. In a particular embodiment, the HepaWash® system (Example 2) is used in the present invention.

Further Process Features and Parameters

The following further features and parameters are suitable for use in connection with the dialysis unit, i.e. in the device comprising the first chamber, the second chamber and the semipermeable membrane. Conventional components of a dialyzer, such as manometers, air detectors, pumping devices like heparin pumps, blood pumps, etc., form part of the means or device according to the invention.

Single-Use

It is possible to discard the dialysis liquid after exit from the second chamber (outlet). Such embodiments are referred to as "single use" or "single pass" process. The single use embodiment requires the addition of fresh dialysis liquid (into the inlet of the second chamber) during essentially the entire duration of the process. Although single use is possible in the context of the present invention, it is not as convenient as the recycling described below. Therefore, single use is less preferred in the context of the present invention.

Recycling

As opposed to single use, the dialysis liquid can also be recycled ("recycling" or "multi use" or "multi pass"). To that end, dialysis liquid ("used dialysis liquid") exiting from the second chamber (outlet) is collected and returned into the second chamber (inlet). Albumin is relatively costly. It is therefore generally desired to recycle albumin-containing dialysis liquid. In other words, the recycling can result in major cost savings. The recycling enables also having a high dialysis liquid flow rate of up to 4000 ml/min.

Typically, recycling of the dialysis liquid requires the cleaning or regeneration of the dialysis liquid. Such cleaning or regeneration is achieved by at least one type of treatment step in order to remove undesired substances from the dialysis liquid (i.e. used dialysis liquid) prior to re-entry into the second chamber. This step normally occurs outside the second chamber, i.e. at a site different from the site of blood contact. The at least one treatment step may feature one or more of exposure to an (i) adsorber and/or (ii) diafiltration and/or (iii) acidic pH and/or basic pH (iv) and/or exposure to a permeable or semipermeable membrane (i.e. a membrane different from the one being localized in the dialysis unit between the first and second chamber). The adsorber is usually an entity different from albumin; i.e. in the case of albumin-containing dialysate, the adsorber is a further or additional adsorber. In particularly suitable embodiments, the adsorber is capable of binding sodium ions ($Na^+$) or chloride ions ($Cl^-$).

Any one or more of such treatment steps can be conducted in row or in parallel (i.e. upon splitting the dialysis liquid). It is possible to foresee that the dialysis liquid is subjected to treatment or purification after being exposed to the blood across the semipermeable membrane, i.e. after exiting from the second chamber. Suitable means for treatment or purification of the dialysis liquid include one or more adsorber unit, one or more pH change unit(s) and/or one or more diafiltration unit. Such units are not mutually exclusive and may be present in row or in parallel. In particular, the recycling of the dialysis liquid of the systems and methods described herein can also require, and thus involve, an adjustment of the (combined) carbonate/bicarbonate concentration and/or of the pH, so as to ensure that the pH of the dialysis liquid, when being (re)introduced into the first chamber, complies with the properties desired in the context of the present invention, as defined herein. Reintroduced refers to the introduction after recycling.

Flow Rates

The blood is passed through the first chamber, and the dialysis liquid is passed through the second chamber. The flow rate, or speed of the blood and of the dialysis liquid may selected from constant or varying (changing) over time.

In general, the blood flow rate in the extracorporeal blood circuit is adjustable between 50 ml/min and 7000 ml/min. However, typically, in the systems and methods described herein, the blood flow rate is about 2 l/min or less, e.g. about 1l/min or less, about 0.5l/min or less, and in any case at least 50 ml/min. The blood flow rate is typically controlled and regulated and may be adjusted to the treatment conditions and to the dialysis liquid flow rate. Thus, the systems and methods described herein make it possible that the lungs can be supported up to 100% with maximum mid-flow blood flow rates, without using another ventilation device. Whereas conventional extracorporeal lung support devices which are mid-flow-treatments cannot support the lungs equally well. This means that the lung support aspects function sufficiently well at mid-flow conditions so that that it is easy to handle for the operator and less hazardous for the patient. Further, an additional lung protective ventilation (LPV), which is common for other mid-flow devices, is dispensable.

In the systems and methods described herein, the dialysis liquid flow rate can be in the range between 10 ml/min and 11000 ml/min (i.e. 0.1667 ml/h to 183.333 ml/h). More typically, the dialysis liquid flow rate is selected among the following: slow dialysis liquid flow rates (1-2 l/h) and normal dialysis liquid flow rates (25-60 l/h)/dialyzer, as well as intermediate rates (more than 2 l/h to less than 25 l/h). The flow rate can thus be adapted as required. In general, it is preferred that the flow rate of the blood is lower than the flow rate of the dialysis liquid. Thereby, an efficient treatment of the blood can be achieved.

In the dialysis unit, i.e. in the device comprising the first chamber, the second chamber and the semipermeable membrane, the blood and the dialysis liquid are conventionally conveyed in counter-current, but they can also be conveyed in co-current. However, in general it is conceivable that blood and dialysis liquid can be passed through the device for dialysis in the same direction or counter-current.

$CO_2$ Removal from the Dialysis Fluid

In a preferred embodiment of the systems and methods described herein, carbon dioxide, and/or carbonic acid and/or its dissociation products ($H^+/HCO_3^-$) may be removed from the dialysis liquid ("removal"). This is ideally foreseen in a discrete step, i.e. a step after the dialysis liquid exits the second chamber (outlet). The means for these purposes are not particularly limited, as long as they are suitable. In these aspects, carbon dioxide, and/or carbonic acid and/or its dissociation products ($H^+/HCO_3^-$) are suitably removed from the dialysis liquid by degasification (pressure reduction, heating or cooling, ultrasonic, membrane degasification, substitution by inert gas, addition of reductant, freeze-pump-thaw cycling, pH decrease, centrifugal force or addition of degasification additives), filtration, sorption or chemical bonding. For example, the removal may be achieved by degasification (e.g. pressure reduction, heating or cooling, ultrasonic, membrane degasification, substitution by inert gas, addition of reductant, freeze-pump-thaw cycling, pH decrease, centrifugal force or addition of degasification additives), filtration, sorption or chemical bonding and/or a combination of such measures. It is ideally possible to measure the concentration of carbon dioxide and/or carbonic acid and/or hydrogen carbonate, and/or to measure the pH, in the dialysis liquid, after exit of the dialysis liquid from the second chamber. The removal of carbon dioxide, and/or carbonic acid and/or its dissociation products is particularly suitable in those embodiments wherein the dialysis liquid is recycled, as described below.

In a particularly suitable embodiment, the process according to the present invention is conducted such that the recycling includes acidification of the dialysis liquid to acidic pH, for formation of carbon dioxide, and removal of carbon dioxide from the dialysis liquid across a carbon dioxide-permeable membrane. Suitably, the membrane is gas-permeable, and carbon dioxide is removed in the gas phase.

Acid/Base Treatment

Albumin is commercially available, but relatively expensive. Therefore, albumin-based dialysis liquids can incur high process costs. In the prior art, recycling of albumin-containing dialysis liquid has been described for the case of liver dialysis, e.g. in WO 2003/094998, incorporated herein by reference in its entirety. As described in WO 2003/094998, albumin can be recycled based on the principle that the binding affinity of carrier proteins (such as albumin) towards bound substances, such as toxins, can be influenced by certain measures, such as pH-changes. The selective decreasing and subsequent increasing (or vice versa) of the pH of a dialysis liquid containing albumin allows for efficient removal of the bound substances, via dialysis (diffusion) or filtration (convection) or a combination of both processes, hereafter called diafiltration. In general, diafiltration is a dilution process that involves removal or separation of components (permeable molecules like salts, small proteins, solvents etc.) of a solution based on their molecular size by using filters permeable of the components. Diafiltration-mediated removal of such components allows for subsequent recycling of the albumin. As described in the prior art, albumin can be efficiently regenerated in a dialysis regeneration unit having two parallel dialysis liquid streams, i.e. an acidic flow path and an alkaline flow path in parallel (see, WO 2009/071103, herein incorporated by reference in its entirety). The process and device (e.g. dialysis liquid regeneration unit, dialysis unit) described in WO 2009/

071103 are also suitable for recycling albumin-containing dialysis liquid in the systems and methods described herein.

In the step of treating (cleaning, regenerating) the dialysis fluid at an altered pH, toxins bound e.g. to albumin can be removed. For efficiently removing said toxins, the dialysis liquid regeneration unit according to the systems and methods described herein features two flow paths that are fluidically connected in parallel. The dialysis liquid to be regenerated is split up and conveyed through the two flow paths. In the first flow path, an acidic fluid is added (from an acidic fluid supply unit) to the dialysis liquid. For toxins that are soluble in acidic solution, the concentration of free toxins in solution is increased. In a detoxification unit, which is located downstream of the acidic fluid supply unit, the free toxins are removed from the acidified dialysis liquid flowing in the first flow path. By adding an acidic fluid to the dialysis liquid, removal of acidic soluble toxins is facilitated. Furthermore, by decreasing the pH, alkaline soluble toxins may e.g. be precipitated and thereby removed from the dialysis liquid fluid. In the second flow path, which extends in parallel to the first flow path, an alkaline fluid is added (from an alkaline fluid supply unit) to the dialysis liquid flowing in the second flow path. Due to the increase of the pH, the concentration of free alkaline soluble toxins is increased, and thus, removal of alkaline soluble toxins is facilitated. These toxins are removed by a further detoxification unit, which is located downstream of the alkaline fluid supply unit. The further detoxification unit is adapted for removing toxins from the alkalized dialysis liquid flowing in the second flow path. Furthermore, by increasing the pH, acidic soluble toxins may e.g. be precipitated and thereby removed from the dialysis liquid fluid. By providing an acidic flow path and an alkaline flow path in parallel, both acidic soluble toxins and alkaline soluble toxins may be efficiently removed from the dialysis liquid. Hence, the dialysis liquid regeneration unit according to embodiments of the systems and methods described herein is capable of efficiently removing protein-binding toxins. The term "toxin" is understood very broadly herein and encompasses all protein-binding substances, even if they normally not directly referred to as toxins, such as drugs, electrolytes, $H^+$, hormones, fats, vitamins, gases, and metabolic degradation products like bilirubin. Downstream of the acid treatment unit and the base treatment unit, together "pH treatment units" (or detoxification units), the regenerated acidified dialysis liquid from the first flow path may be merged with the regenerated alkalized dialysis liquid from the second flow path, whereby the acidified dialysis fluid from the first flow path and the alkalized dialysis fluid from the second flow path may neutralize one another at least partially. Hence, by merging the flow of acidified dialysis liquid from the first flow path with the flow of alkalized dialysis liquid from the second flow path, a flow of regenerated dialysis liquid at a physiological pH value may be provided.

According to a preferred embodiment, the acidic fluid added by the first supply unit contains at least one of hydrochloric acid, sulfuric acid, and acetic acid. In a preferred embodiment, the first supply unit is adapted for adjusting the pH of the dialysis liquid in the first flow path to a pH between 1 and 7, preferably between 2.5 and 5.5.

Preferably, the alkaline fluid added by the second supply unit contains at least one of sodium hydroxide solution and potassium hydroxide solution. In a preferred embodiment, the second supply unit is adapted for adjusting the pH of the dialysis liquid in the second flow path to a pH between 7 and 13, preferably between 8 and 13, more preferably between 8 and 11.

Further preferably, the acidic fluid and the alkaline fluid are chosen such that "physiological" neutralization products are generated during neutralization. For example, a certain concentration of the formed neutralization products might already be present in the respective biological fluid anyway. For example, when using aqueous hydrochloric acid and aqueous sodium hydroxide solution, a certain concentration of NaCl is produced during neutralization of the acidified flow and the alkalized flow. NaCl is typically also present in a biological fluid, like e.g. blood or blood serum.

According to a preferred embodiment, by decreasing the pH of the dialysis liquid in the first flow path, a concentration ratio of toxin-carrier-complex to free toxin and free carrier substance is shifted in favour of the free toxin for at least some of the toxins in the dialysis liquid, thereby increasing a concentration of free toxins in the dialysis liquid. By decreasing the pH of the dialysis liquid in the first flow path, the solubility of acidic soluble toxins (like e.g. magnesium or copper) is increased, whereas the binding affinity between the acidic soluble toxins and the carrier substances is reduced. Accordingly, the concentration of free toxins in solution is increased.

Further preferably, the detoxification unit is adapted for at least partially removing said free toxins. Due to the increased concentration of free toxins, said toxins may be removed at an increased rate.

Furthermore, by decreasing the pH value of the dialysis liquid in the first flow path, some of the alkaline soluble toxins may e.g. be precipitated and thereby removed from the dialysis liquid fluid.

In a preferred embodiment, by increasing the pH of the dialysis liquid in the second flow path, a concentration ratio of toxin-carrier-complex to free toxin and free carrier substance is shifted in favor of the free toxin for at least some of the toxins in the dialysis liquid, thereby increasing a concentration of free toxins in the dialysis liquid. By increasing the pH of the dialysis fluid in the second flow path, solubility of alkaline soluble substances (like e.g. bilirubin) is increased, whereas the binding affinity between the alkaline soluble toxins and the carrier substances is reduced. Accordingly, the concentration of free toxins in solution is increased.

Preferably, the further detoxification unit is adapted for at least partially removing said free toxins. Due to the increased concentration of free toxins, said toxins may be removed at an increased rate.

Furthermore, by increasing the pH value of the dialysis liquid in the second flow path, some of the acidic soluble toxins may e.g. be precipitated and thereby removed from the dialysis liquid fluid.

According to a further preferred embodiment, by increasing the temperature of the dialysis liquid, the concentration ratio of toxin-carrier-complex to free toxin and free carrier substance is shifted in favour of the free toxin for at least some of the toxins in the dialysis liquid, thereby increasing a concentration of free toxins in the dialysis liquid. Accordingly, the free toxins may be removed at an increased rate by the detoxification units.

Further aspects of the recycling of albumin-containing dialysis liquid are described in WO 2009/071103, incorporated herein by reference in its entirety, including illustrations in the figures. In addition to the findings described in WO 2009/071103, albumin has also contributes to the excellent buffering capacity of dialysis liquids according to the present invention.

Adsorber Treatment/Adsorption

In order to extract or remove excess or undesired substances, like electrolytes (e.g. cations such as potassium, sodium and calcium cations; or anions, such as chloride, carbonate or bicarbonate cations), an adsorber can be brought in contact with the dialysis liquid. In general, the adsorber is capable of adsorbing at least one undesired substance present in the patient's blood (e.g. urea, uric acid, electrolytes, sodium, calcium or potassium cations; chloride anions). Typically, an adsorber is present in an adsorber unit, i.e. a stationary unit through which the dialysis liquid is passed. The type or composition or material of the adsorber is not particularly limited, as long as it has the capacity to bind at least one of the substances to be removed from the dialysis liquid. Different adsorber types are known in the art. By appropriate choice of the adsorber, the process can be adjusted to the actual needs, e.g. needs of an individual patient. An adsorber is particularly useful in recycling embodiments, i.e. when it is intended to recycle the dialysis liquid.

Aspects of Regeneration of the Dialysis Liquid

Excess or undesired substances can be removed from the dialysis liquid (used dialysis liquid) across a membrane, i.e. a permeable or semipermeable membrane. For example, gases and/or solutes/ions dissolved in the dialysis liquid can be removed by such a membrane treatment. In a preferred embodiment, carbon dioxide is removed, either as a gas or in the state of being dissolved in a liquid. One particularly suitable way of removing carbon dioxide consists of bringing the dialysis liquid into contact with a membrane which is permeable for carbon dioxide. The dialysis liquid has a certain pressure $p_1$, and the pressure of the fluid (liquid or gas) on the other side of said membrane, $p_2$, is lower, i.e. $p_2 < p_1$. The object of $CO_2$ removal from the used dialysis liquid can also, or alternatively, be achieved if the partial pressure of $CO_2$ is lower in the fluid on the other side of said membrane. Similarly, it is possible to remove hydrogen carbonate along a concentration gradient, i.e. by bringing the used dialysis liquid into contact with a bicarbonate-permeable membrane, as long as the (combined) carbonate/bicarbonate concentration in the fluid (liquid) on the other side of the membrane is lower than the (combined) carbonate/bicarbonate concentration of the used dialysis liquid. In any case, the membrane used is not permeable for albumin. This can be realized by selecting a membrane with an appropriate pore size. Such membrane treatment is particularly useful for recycling embodiments.

Dialysis Units

Preferably two devices for dialysis, or two dialysis units, are used in parallel. This allows for increase of the exposed membrane surface area, and thus for more efficient exchange of the one or more undesired substance across the semipermeable membrane.

Therapeutic Uses

It is possible and desired to beneficially use the systems and methods described herein for medical purposes. Any activity directed at treatment of the human or animal body by surgery or therapy, particularly those aiming at preventing or improving a condition in a living subject, i.e. serving a medical purpose, may be referred to as a medical method or medical use. In general, the terms method and process are used interchangeably herein. Sometimes, however, the term method is used to refer particularly to medical methods; the medical methods of the present invention can involve any and all aspects of the above described process for removal of an undesired substance from blood. In particular, this invention provides a method for extracorporeal treatment of blood from a patient in need of such treatment. The extracorporeal blood is subjected to dialysis process as described herein, i.e. is exposed to a dialysis liquid across a semipermeable membrane. For this purpose, blood is removed from a subject, subjected to the systems and methods described herein, and suitably returned to the subject. In general, in such methods, venous blood from a patient is removed and entered into the first chamber of the process of the present invention. This allows for treatment of the blood in the systems and methods described herein, in any and all aspects described herein. Subsequently, the blood ("treated blood") exits the first chamber and can be returned to the patient. The treated blood most typically is entered into a vein of the patient, but can alternatively be returned into an artery, however the latter is suitably limited to processes wherein the blood is also subjected to oxygenation. All these aspects spanning the process from removal of patient blood from the body until returning treated patient blood into the body are common to medical the methods for all indications described herein.

The systems and methods described herein are useful for treatment of the human or animal body by therapy (generally referred to as medical uses). It is possible to customize the therapeutic uses of the present invention specifically to the actual needs of the respective patient. Although, in nature, gas-exchange is not limited to organisms having lungs, but equally occurs in organisms having gills, such as fish, the therapeutic uses of the present invention are focused at the goal of lung support, i.e. for treating or preventing certain conditions in organisms having lungs, such as preferably mammals, and more preferably humans. Therefore, gills or organisms having gills, are not discussed in detail in this specification.

Preferably, in the therapeutic methods, the dialysis liquid is characterized by an osmolarity which is substantially identical to the osmolarity of blood, i.e. of the blood of the species (e.g., human) being dialyzed in the dialysis unit.

Optionally, the systems and methods described herein, although suitable for extracorporeal treatment of blood, do not feature an invasive step and do not feature a step representing a substantial physical intervention on the body and do not feature a step requiring professional medical expertise to be carried out and do not feature a step involving a substantial health risk even when performed with the required professional care and expertise. Preferably, the systems and methods described herein do not feature an invasive step representing a substantial physical intervention on the body that requires professional medical expertise to be performed and that involves a substantial health risk even when carried out with the required professional care and expertise. For example, the systems and methods described herein optionally do not feature an invasive step of connecting or disconnecting a dialysis system with the human or animal body. In another example, the contacting of an extracorporeal device to the venous blood of the living subject, and thus the respective medical method, does not entail a substantial health risk.

The therapeutic methods of the present invention are useful or suitable for treating at least one condition from among respiratory acidosis, metabolic acidosis, lung failure, kidney failure, multi-organ failure and combinations of any one or more of these. The therapeutic methods can be optimized to the condition to be treated or to the individual to be treated in particular (personalized medicine). While the following sections discuss the treatment of these conditions, respective methods of prevention are equally encompassed by the present methods.

All these treatment methods involve withdrawing venous blood from a subject thus yielding extracorporeal blood, exposing the extracorporeal blood to contact with the dialysis liquid as described herein across a semipermeable membrane thus yielding treated blood, and returning the treated blood into the same subject, preferably into the vein of the subject, and in a less preferred embodiment into the artery of the subject. Particular configurations are described in the following.

Treating Respiratory Acidosis

The systems and methods described herein are suitable for treating patients suffering from acute or chronic respiratory acidosis. Patient groups include subjects suffering from hypoventilation, lung tumors, asthma, muscular dystrophy or emphysema, particularly late-stage emphysema. For the treatment of subjects suffering from respiratory acidosis, the dialysis liquid, at the stage of entering the second chamber, suitably contains a (combined) carbonate/bicarbonate concentration in the range from 0 to 40 mmol/l. In fact, for respiratory acidosis, the preferred (combined) carbonate/bicarbonate concentration is as low as possible, i.e. 0 mmol/l or more than 0 mmol/l. Subranges include 1 to 35 mmol/l, 2 to 30 mmol/l, 3 to 25 mmol/l, 4 to 20 mmol/l, 5 to 15 mmol/l, e.g. 10 mmol/l.

In general, a (combined) carbonate/bicarbonate concentration at the lower end of the above range or subrange allows for efficient removal of withdrawal of undesired substances, such as bicarbonate, $CO_2$ and carbonate, from the blood.

When the (combined) carbonate/bicarbonate concentration in the dialysis liquid is low (e.g. 0 mmol/l or 0 to 10 mmol/l), then the buffering is suitably achieved by sufficient amount of other buffering agents in the dialysis liquid, typically albumin and/or Tris. Particularly, when no carbonate/bicarbonate is added to the dialysis liquid (i.e. the carbonate/bicarbonate concentration in the dialysis liquid is 0 mmol/l or near 0 mmol/l), then it is preferable that both Tris and albumin are present in the dialysis liquid. The concentrations of these buffering agents are selected such that the buffering capacity exceeds the buffering capacity of blood plasma. This allows for efficient adjustment of the blood pH.

It is also possible to increase the (combined) carbonate/bicarbonate concentration over the course of treatment. This allows to adapt the treatment to the needs of an individual (personalized medicine).

Following exposure to such dialysis liquid across the semipermeable membrane, the blood typically has a pH in the range of 7.40 or more; such as higher than 7.40 but not higher than 8.0, such as pH 7.5 to 7.9, or pH 7.6 to 7.8, or pH 7.65 to 7.75, e.g. 7.7. Such blood is returned into the subject.

The dialysis liquid is either discarded, or, preferably, recycled. In the latter case it is preferable to subject the dialysis liquid to a membrane treatment. By the membrane treatment, carbon dioxide and/or bicarbonate and/or carbonate and/or carbonic acid may be removed, or partially removed. This allows for recycling of the dialysis liquid. For removal of carbon dioxide, the membrane treatment is preferably carried out at low pH, i.e. following acidification of the dialysate.

It is known that, in subjects suffering from respiratory acidosis (i.e. excess dissolved $CO_2$ in the body fluids due to inefficient removal in the lungs), the kidney oftentimes reacts, with some delay of e.g. 3 weeks, by production of increased amounts of bicarbonate. The systems and methods described herein allow treating subjects suffering from respiratory acidosis during the entire course of the disease, i.e. at early stages when mainly the removal of excess $CO_2$ from the body fluids is desired, as well as at later stages, when (additionally) the removal of excess bicarbonate from the body fluids is desired. Further, the removal of excess $H^+$ ions from the body fluids is possible at all stages of the disease. During the course of treatment, the physician can alter the composition and pH of the dialysis liquid based on the guidance provided herein.

Treating Metabolic Acidosis

For the treatment of subjects suffering from acute or chronic metabolic acidosis, with normal lung function, the dialysis liquid, at the stage of entering the second chamber, suitably contains a (combined) carbonate/bicarbonate concentration in the range from 20 to 40 mmol/l, preferably 25 to 35 mmol/l, more preferably exactly or about 30 mmol/l.

For the treatment of subjects suffering from acute or chronic metabolic acidosis, but with impaired lung function, the dialysis liquid preferably does not contain added carbonate/bicarbonate. A suitable dialysis liquid for that type of patients suitably contains a (combined) carbonate/bicarbonate concentration in the range from 0 to 5 mmol/l (preferably 0 mmol/l), and the buffering capacity is contributed by albumin and Tris, both within the concentration ranges defined above. For example, if the (combined) carbonate/bicarbonate concentration in the dialysis liquid were identical to the (combined) carbonate/bicarbonate concentration in the patient's blood, no net transfer of bicarbonate would be expected.

A high pH of the dialysis liquid is desired, e.g. pH 8.0 to 11.0, preferably pH 9.0 to 10.0. The buffering capacity of the dialysis liquid is higher than the buffering capacity of blood plasma. The combination of high pH of the dialysis liquid and high buffering capacity of the dialysis liquid allows for efficient adjustment of the blood pH, and minimal net flux (addition or removal) of substances of bicarbonate, $CO_2$ and carbonate from the blood. In particular, the flux can be increased compared to standard dialysis methods.

Following exposure to such dialysis liquid across the semipermeable membrane, the blood typically has a pH in the range of desired to adjust the blood pH to a range or value encompassing that range, i.e. 7.0 to 7.8, 7.2 to 7.6, or 7.3 to 7.5, 7.35 to 7.45, and most preferably exactly or about 7.40.

The systems and methods described herein also allow for the treatment of a condition characterized by a combination of respiratory acidosis and metabolic acidosis. This is possible because the dialysis liquid, particularly the pH and the (combined) carbonate/bicarbonate concentration in the dialysis liquid, can be adjusted to individual needs.

Treating Lung Failure

The systems and methods described herein are suitable for treating patients suffering from acute or chronic respiratory failure (lung failure). Subjects suffering from lung failure, but typically not from failure of other organs, such as kidney failure or liver failure, develop respiratory acidosis, or are at risk of developing respiratory acidosis. This is because removal of carbon dioxide does not occur as efficiently as in healthy subjects, or does not occur at all. This patient group includes patients suffering from asthma, hypoventilation, lung diseases such as lung cancer, complications associated with smoking and with exposure to other air-born toxins or particles, or muscle dystrophy, or emphysema, particularly late-stage emphysema. Many patients suffering from such lung diseases have a completely working kidney (full renal function). The systems and methods described herein provide a lung support. Subjects suffering from such conditions are suitably treated by the systems and methods described herein as described for the treatment of respiratory acidosis.
Treating Combined Organ Insufficiencies: Combined Support of the Lungs, Liver and Kidney In many cases subjects suffering from lung failure are also affected by a liver or kidney dysfunction. The methods of the present invention are also suitable for treating such subjects, and thus to support these organs:
Treating Combined Lung and Kidney Failure The systems and methods described herein also allow treating subjects suffering from acute or chronic kidney (renal) insufficiency, or chronic renal failure (CRF). In general, the kidneys play an important role in maintaining acid-base homeostasis of healthy individuals by regulating the pH of the blood plasma: main functions include reabsorption of bicarbonate from urine, and excretion of hydrogen cations into urine. These functions of the kidneys are important for maintaining acid-base balance, and can also contribute to controlling blood pH. The proper functioning of the kidneys is affected in patients suffering from kidney failure. This patient group includes patients suffering from kidney diseases such as kidney cancer, as well as complications associated with intoxication and with exposure to certain medicaments.

Renal replacement therapy (RRT) is being widely used in modern intensive care settings/intensive care unit (ICU) for treating such subjects. In subjects in the intensive care unit (ICU subjects), acute renal failure (ARF) is frequent, as a part of multiple organ dysfunction syndrome (MODS), in postoperative states and after interventional studies, in already susceptible individuals. In general, ICU subjects are in need of different organ support such as continuous renal replacement therapy (CRRT), liver dialysis and mechanical ventilation. In contrast to the state of the art, which traditionally requires at least three different devices for the treatment of kidney, liver and lung failure in such subjects (or, in addition to a device for the treatment of liver failure, a combined three-chamber device for the treatment of kidney/lung failure, PrismaLung™, DE 10 2009 008601 A1; Novalung, WO 2010/091867, the disclosures of which are herein incorporated by reference in their entireties), the systems and methods described herein provide a significant improvement.

The conditions ((combined) carbonate/bicarbonate concentration of the dialysis liquid entering the second chamber; pH of the blood exiting the first chamber . . . ) are suitably selected among the conditions described above for any of respiratory or metabolic acidosis, preferably those described for metabolic acidosis. Additionally, it is preferable to include an adsorber, as generally described above. The adsorber is suitable for binding or adsorbing at least one undesired substance present in the patient's blood. To extract liquid or dissolved substances (urea, uric acid, electrolytes, sodium, calcium or potassium cations; chloride anions). For example, in patients suffering from kidney failure, it is typical that the kidney fails to maintain physiological concentrations of sodium, calcium or potassium cations; and/or of chloride anions, in the blood. These deficiencies are addressed by the systems and methods described herein.
Treating Combined Kidney, Liver, and Lung Failure The systems and methods described herein also allow for treating subjects suffering from acute or chronic liver failure in addition to lung failure, kidney failure, or both. Typical treatment using the systems and methods described herein involves extracorporeal toxin removal. For the treatment of such subjects, the methods described in WO 2009/071103 and/or WO 03/094998, the disclosures of which are herein incorporated by reference in their entireties, or the methods made available through the company HepaWash, GmbH (Munich, Germany), can be modified such that the dialysis liquid complies with the framework dialysis liquid of the systems and methods described herein, or with any embodiments thereof. In such methods, albumin has a dual or synergistic function: it not only binds toxins (which addresses liver insufficiency) but also buffers the dialysis liquid, together with carbonate (which addresses lung insufficiency). That means, that in addition to the functionalities described in WO 2009/071103 and WO 03/094998, it is possible to perform a lung support and/or to correct the blood pH to a physiological level or otherwise desired level. This treatment allows combining a kidney dialysis, liver dialysis and a lung support featuring a carbon dioxide removal and blood oxygenation in one single device. Modifications or configurations described above for the treatment of kidney failure, such as presence of an adsorber, are suitably employed also in this embodiment.

It is also possible to gradually increase the (combined) carbonate/bicarbonate concentration over the course of treatment, within the range of the present invention (0 to 40 mmol/l).
Automatic and Patient Adapted $CO_2$ Removal The systems and methods described herein may be adapted for automatically measuring certain gas values present in a biological fluid such as blood, such as blood pH, $pCO_2$ and bicarbonate concentration, without contact with that biological fluid. Accordingly, the dialysate fluid composition may be readily and rapidly adapted as needed or desired in an automatic manner.

$CO_2$ is transported in the blood mostly as $H^+ + HCO_3^-$. In order to remove $CO_2$ or to treat an acid/base imbalance or disturbance completely in a liquid phase, it is necessary to remove $H^+$ and $HCO_3^-$ from the biological fluid, such as blood, of a patient through the dialysis fluid itself. The pH of the dialysis fluid should be higher than the pH of the blood, and the $HCO_3^-$ concentration in the dialysis fluid should be lower than the concentration in the blood. $OH^-$ in the dialysate eliminates the protons in the blood. Referring to FIGS. 1 and 2, bicarbonate concentration in the dialysis system can be adjusted by adding different amounts of bicarbonate through the fluids, for instance, at points 21 and 22, or removing liquid (such as dissolved bicarbonate) or gas (bicarbonate+$H^+ \rightarrow CO_2$ so that in the acid path gas can be removed to extract bicarbonate) through the filters 30 and 31 by the pumps 32 and 33 into the waste bags 36 and 37.

When the blood gas values of the subject undergoing treatment are known, the systems and methods described herein can automatically adjust the compositions of the dialysis fluid, such as pH and bicarbonate concentration in accordance with treatment goals and to meet the subject's needs. Thereby, the systems and methods described herein may be adapted to relatively continuously show a patient's blood gas values. This effectively eliminates the need for repeated blood samples necessary to determine the blood gas values of the patient.

The dialysis fluid composition and preferred values are described herein. In effect, for a dialysis fluid according to the presently described systems and methods, the following values are known from the beginning of the method: pH, $pCO_2$, $HCO_3^-$ bicarbonate concentration, and buffering capacity. Other values may easily be calculated by those of ordinary skill in the art according to the Henderson-Hasselbach equation.

Referring to FIGS. 1 and 2, the pH of the subject liquid may be measured using various pH meters 11, 12, 13, 14, and 15. The bicarbonate concentration may be measured by a reverse titration of the dialysis fluid. Bicarbonate functions as an important buffer in the dialysate along with albumin. The albumin concentration and its buffering capacity at different pH values are known because the dialysis system as described herein is a closed system, and the concentration of albumin at the beginning of the dialysis method is known.

Referring to FIGS. 1 and 2, liquid may be removed through filters 30 and 31. Albumin cannot pass through the semipermeable membrane of these filters nor through membrane 6. Dialysate from the dialyzer 5 with a known pH 12, 13, the flow 4, of which, goes to 16 where it is split into two flow paths. An acid solution 21 is provided and mixed with osmosis water 20 with the resultant fluid 25 having a defined and known concentration of $H^+$ is mixed at 27 with the dialysis fluid. The flow rate of 25 is known and determined according to the needed pH for the liquid at position 3 as measured by pH sensor 11. The pH sensor 14 measures the pH necessarily maintained at a relatively constant level for good toxin removal, e.g. pH 3. The pH is achieved by a variable flow rate with the pump 17. Hence, according to the flow rate that can be measured at sensor 14 and optionally adjusted at pump 17, flow may be adjusted to achieve a defined pH and addition of a known concentration of protons at 25. The buffering capacity of the dialysis fluid may be calculated because the only unknown buffer in the liquid is bicarbonate. The calculation features determining the pH decrease from pH sensors 12 and 13 to pH sensor 14, determining the volume of liquid flowing according to pump 17, and determining the concentration of $H^+$ at position 25.

Dialysate from the dialyzer 5 with a known pH 12, 13, the flow 4, of which, goes to 16 where it is split into two flow paths. A base solution 22 is provided and mixed with osmosis water 19 with the resultant fluid 26 having a defined and known concentration of $OH^-$ is mixed at 28 with the dialysis fluid. The flow rate of 26 is known and determined according to the needed pH for the liquid at position 3 as measured by pH sensor 11. The pH sensor 15 measures the pH necessarily maintained at a relatively constant level for good toxin removal, e.g. pH 11. The pH is achieved by a variable flow rate with the pump 18. Hence, according to the flow rate that can be measured at sensor 15 and optionally adjusted at pump 18, flow may be adjusted to achieve a defined pH and addition of a known concentration of protons at 26. The buffering capacity of the dialysis fluid may be calculated because the only unknown buffer in the liquid is bicarbonate. The calculation features determining the pH increase from pH sensors 12 and 13 to pH sensor 15, determining the volume of liquid flowing according to pump 18, and determining the concentration of $OH^-$ at position 26.

The systems and methods described herein thereby provide a relatively continuous two way titration effective to calculate the bicarbonate concentration in the dialysis fluid. This bicarbonate concentration is the concentration of bicarbonate in the liquids 2 and 4 (see, FIGS. 1 and 2). Essentially, the entire buffering capacity of the dialysate is known.

$H^+$, $HCO_3^-$ and $OH^-$ can diffuse and exchange through the semipermeable membrane 6. If the flows of 1 and 3 are concurrent, and the flowrates are similar or the ratio of both flows and the exchange rates are known, there may be a complete exchange or adaptation of the concentrations. Hence, the measured pH sensor 12 and the calculated bicarbonate concentration are the same as in the liquid 2.

If the pH and the bicarbonate concentration are known, the pH and the bicarbonate concentration of the liquid 2 may be used to calculate the $pCO_2$ of the liquid according to the Henderson-Hasselbach equation. The equation for blood is as follows:

$$pH = 6.1 + \log_{10}\left(\frac{[HCO_3^-]}{0.03 \times pCO_2}\right)$$

It is also possible to measure the $pCO_2$ with the sensor 12 to obtain a redundant measurement of the values. Then, it is easy to calculate the bicarbonate concentration according to the Henderson-Hasselbach equation.

If the buffering capacity of the dialysate is too high or the flow rates are too different, the pH of the liquid 4 and 2 may not be the same. However, the bicarbonate concentrations in 2 and 4 will be the same (flowrate 2 to 4 max 1 to 12). It is thus easy to calculate the pH of liquid 2 with the equation above, whereby the $pCO_2$ is either measured by sensor 12 or 10. Sensor 10 may be integrated into the system or an external analyst system where the values of the external system are entered into the dialysis system by the user.

An important objective of the dialysis systems and methods described herein is to adjust the acid base balance of the liquids 1 and 2, e.g. blood from a patient. Protons may be considered as toxins in the liquids 1, 2. It is desirable to determine quantitatively the amount of toxins removed. Between the sensors 11 and 12 a ΔpH may be measured if there is an exchange between the liquids on both sides of the semipermeable membrane. The buffering capacity of the dialysis liquid is known because of the continuous titration with acid and base at 27 and 28. With the known buffering capacity of the dialysate and the ΔpH between the pH of the fluids entering the dialyzer or in 11 and the pH of the fluids exiting the dialyzer or out 12 pH measurements, the amount of protons removed from the blood can be easily calculated. Thereby the proton loads of the blood and the patient are continuously measured. In accordance to that proton loads determined, the pH of the dialysate can be adjusted to remove more or less protons from the blood as desired or needed.

By having a higher, e.g. pH 9, and a lower, e.g. pH 7.4, at the dialyzer input 11 for a relatively short time, the potential of removing more or less protons from the blood is known. Therefore, if the amount of protons removed or ΔpH between the inflow 11 and the outflow 12 is small, the dialysate pH should be decreased to prevent an undesired physiological too high pH of the liquid outflow 2 as determined at sensor 10. If the amount of protons removed or ΔpH between the dialyzer inflow 11 and the dialyzer outflow 12 is high, the pH of the liquid 3 can be raised in order to remove more protons from the blood. These tests or determinations of higher and lower pH values may be performed substantially continuously for a very short time, e.g. 1 minute, 10 minutes, or 30 minutes in order to adjust the dialysate pH. For the pH adjusting or calculation of the proton load which has to be removed from one side of the membrane 6, the dialysate the flow rate through both chambers of the dialyzer 5 on each side of the membrane 6 and the buffering capacity of the dialysate must be considered.

The systems and methods described herein also make it possible to calculate the base excess of the patient. Comparison of the base excess with a reference range assists in determining whether an acid/base disturbance is caused by a respiratory, metabolic, or mixed metabolic/respiratory pathology. Evaluating the acid-base status and blood gases in metabolic and respiratory disorders provides valuable information in diagnosing, for instance, circulatory failure, shock, ventilation disturbances, lung perfusion, renal insufficiency, comatose conditions, deranged diabetes mellitus, intoxications, and disturbances of the adrenal cortex function.

Referring again to FIGS. 1 and 2, the pH of the dialysate 3 is adjusted by a different ratio between the concentrations $H^+/OH^-$ of the liquids 25 and 26. Treatment methods are preferably performed concurrent with measurement and calculation of the pH of the liquids. However, these calculations may also be made in counterflow which is more common for dialysis. Under such circumstances, the pH and bicarbonate concentrations are not the same in the liquids on each output side as the flows go opposite directions. But the proton load removed from the patient still can be calculated. As there is a risk for higher pH values on the outflow 2, e.g for the blood, which returns to the patient, it is preferred that at least one parameter of pH, $pCO_2$, $HCO_3^-$ bicarbonate be measured with a sensor 10 before the liquid returns to the patient.

There may optionally be provided a bypass of the dialyzer 5 for the liquid 3. This bypass may be switched from time to time. The goal of the bypass is to double check both sensors 11 and 12 if they are redundant. If there is no exchange through the membrane 6, no bicarbonate except the one added to the system through the liquids 19, 20, 21, 22, 42, 43 or any further solution is added to the dialysate. The bicarbonate concentration in the dialysate can then be adjusted to a defined and known level e.g. zero. Thus, it is also possible to check the buffering capacity of the dialysate especially albumin except bicarbonate during the treatment.

Temperature and Flow

Referring again to FIGS. 1 and 2, sensors 9 and 10 may also be a flow sensor. Such a flow sensor is helpful to perform a better treatment and adjusts the values more exactly. Flowrates of the biological fluid or liquid 1 and 2 in the external circuit are not exactly known. Mostly peristaltic or centrifugal pumps are used so the flow rates are not so exact known and pressure dependent. Sensors 9 and 10 may also be temperature sensors. The pH, chemical reactions and the amount of dissolved gases are temperature dependent.

Measuring Waste Fluids

The systems and methods described herein feature a closed recirculation circuit. Portions of the dialysis fluid are replaced continuously. As such, fresh liquids with known concentrations are introduced into the dialysis circuit at, referring to FIGS. 1 and 2, for instance, 19, 20, 21, 22 while concurrently portions of the recirculating dialysis fluid are removed through, for instance, filters 30, 31. An advantage of using such filters is the pore size of the membrane of the filters 30, 31. It is preferred to use a membrane that is impermeable for albumin. Such waste fluid can be measured with sensors 34 and 35. Therefore, for measuring the bicarbonate concentration, measuring the pH and $pCO_2$ or also titration are valuable since the other main buffer albumin is not in the liquid. It is also advantageous that the measured liquid does not reenter into the circuit so that it can be treated in a different way not allowed for liquids contact the blood again.

Capnography/Skin Measurement

Referring to FIG. 1, with sensor 46 it is possible to measure the $CO_2$ of the patient in the breathing gases. So by capnography which may be performed by infrared spectroscopy, the partial pressure or volume % of $CO_2$ may be measured. With sensor 47 it is possible to measure the $CO_2$ of the patient, for example on the skin. Also, the $pCO_2$, $tcpCO_2$, $SpCO_2$, $pO_2$, $tcpO_2$, $SpO_2$, pulse and temperature may be measured. Such a sensor on the skin or sensing expiration can be used to measure the $pCO_2$ of the patient. These values may be analyzed by a controller 45 of the dialysis system. The missing carbon dioxide that is not exhaled, e.g. because of a lung failure, may be extracted in the extracorporeal dialysis circuit. By knowing the buffering capacity of the dialysis liquid, the flow rates of the blood and dialysate through the dialyzer and in accordance to the Δ between the pH of the dialysis liquid entering the dialyzer and the pH of the dialysis liquid leaving the dialyzer, the needed pH values can be adjusted to extract the exact amount of acid from the blood.

EXAMPLES

The following examples are provided for illustrative purposes. These examples do not limit the invention.

Example 1

Determining Buffering Capacities of Aqueous Solutions Containing Buffering Agents The buffering capacities of various aqueous solutions comprising one or more buffering agents were experimentally tested. These aqueous solutions are model liquids, the buffering capacity of which corresponds either to dialysis liquids (dialysates) according to the present invention or to dialysis liquids (dialysates) for reference purposes.

1A: Preparation of Liquids

These model liquids were generally prepared as described following. For the preparation of model liquids according to the systems and methods described herein and of reference model liquids, pure water (osmosis quality) was used as a basis, and one or more buffering agents according to the systems and methods described herein (albumin and/or sodium bicarbonate ("soda") and/or Tris(hydroxymethyl) aminomethane (Tris/THAM) was added. In particular, albumin (at the concentration indicated below) and/or bicarbonate (at the concentration indicated below) and/or Tris (at the concentration indicated below) was dissolved in water. Subsequently or simultaneously, the pH was adjusted to the values indicated below. If necessary, addition of albumin and adjustment of pH can be done simultaneously. In some instances, albumin dissolves more rapidly at or near the desired pH values as indicated in the Table below. At any rate, the pH is checked, and if necessary adjusted, after all the buffering agent(s) has dissolved. Adjustment of the pH is typically done by addition of an acidic concentrate (aqueous HCl) and/or by addition of a basic concentrate (aqueous NaOH).

For reference, solutions were prepared to which no buffering agent (albumin, carbonate/bicarbonate, Tris) was added. The pH of these solutions was adjusted to 7.45 and 9, respectively, as indicated in the Table below. For further reference, two acetate-containing model liquids, additionally containing sodium bicarbonate, within the range described in the prior art were prepared. For details, see the Table below.

Additionally, four Tris-containing model liquids were prepared. To that end, two solutions of Tris(Tris(hydroxymethyl)-aminomethane) were prepared:

Tris 38 mmol/l: initial pH after dissolution: pH 10.45.

Tris 20 mmol/l: initial pH after dissolution: pH 10.14.

HCl (0.1 M or 0.2M) was added until the pH value indicated in the below table (pH 7.45 or pH 9.0, respectively) was reached, as indicated in the table below. Thereby, Tris-containing model liquids were prepared.

In general, when the model liquids were prepared, carbonate (e.g. sodium carbonate) was not added. However, it is understood that carbonate and bicarbonate are present in dynamic equilibrium, as a function of the pH. Therefore, a model liquid made by addition of a certain amount of bicarbonate (e.g. 20 mmol/l) and adjustment to a certain pH (e.g. pH 9) will comprise a certain combined concentration of bicarbonate and carbonate (e.g. in that case 20 mmol/l).

The following model liquids were prepared:

| Buffering agent | pH | Comment (if any) |
|---|---|---|
| no buffering agent | pH 7.45 | Reference: no buffering agent |
| no buffering agent | pH 9.0 | Reference: no buffering agent |
| 20 g/l albumin | pH 7.45 | Reference |
| 20 g/l albumin | pH 9 | Reference |
| 20 mmol/l sodium bicarbonate (soda) | pH 7.45 | |
| 20 mmol/l sodium bicarbonate (soda) | pH 9 | |
| 20 mmol/l sodium bicarbonate (soda) + 20 g/l albumin | pH 7.45 | |
| 20 mmol/l sodium bicarbonate (soda) + 20 g/l albumin | pH 9 | |
| 38 mmol/l sodium bicarbonate (soda) + 4 mmol/l acetic acid | pH 7.6 | Reference: model liquid within the range described in the prior art |
| 20 mmol/l sodium bicarbonate + 4 mmol/l acetic acid | pH 7.25 | Reference: model liquid within the range described in the prior art |
| 20 mmol/l Tris | pH 7.45 | |
| 20 mmol/l Tris | pH 9 | |
| 38 mmol/l Tris | pH 7.45 | |
| 38 mmol/l Tris | pH 9 | |

Figure 3:
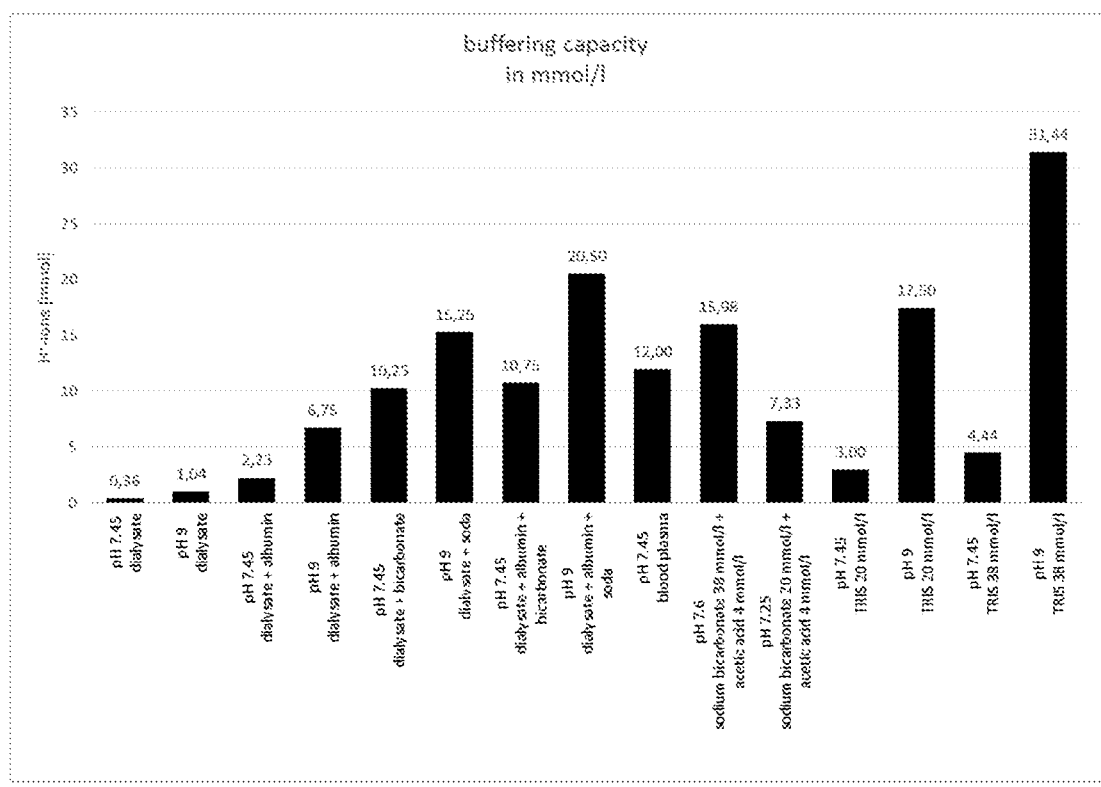
FIG. 3 demonstrates the buffering capacity of solutions comprising bicarbonate and/or albumin as described in Example 1.

In FIG. 3, all these liquids are referred to as "dialysate". The respective buffering agent(s) and pH are indicated.

As a reference (internal standard), the buffering capacity of blood plasma ("plasma") was determined. For that purpose, pig blood was tested as follows. First, the bicarbonate concentration and pH were determined, and it was found that the mean bicarbonate concentration was 24.2 mmol/l and the pH was 7.45. Second, said blood was subjected to centrifugation in order to obtain a cell free supernatant. The cell free supernatant was designated plasma. In FIG. 3, this is referred to as "blood plasma".

1B: Determination of Buffering Capacity

The buffering capacity for $H^+$ ions of all liquids described in section 1A (model liquids according to table of section 1A; plasma as described in section 1A) was experimentally tested. To that end, all liquids (reference model liquids and model liquids according to the present invention, and blood plasma) were subjected to titration with HCl. In particular, 0.1 M HCl was added, the pH was continuously monitored, the solutions were agitated to ensure mixing, and titration was terminated when the pH reached a final value of pH of 6.5. In other words, titration was stopped when the pH reached a value of 6.5. Based on the amount of HCl added until pH 6.5 was reached, the buffering capacity ($H^+$-ion in mmol/l) was calculated.

The buffering capacity determined by this assay is shown in FIG. 3. The buffering capacity of blood plasma was determined to be 12.00 mmol/l $H^+$-ions. It is preferred that model liquids according to the present invention are characterized by a buffering capacity (in mmol/l) superior to the buffering capacity of blood plasma, as determined by this assay. Thus, the model liquid according to the systems and methods described herein provides excellent buffering capacity, particularly in embodiments wherein the model liquid has a pH above the pH of normal human blood.

Example 2

Comparison of the Systems and Methods Described Herein to a Reference Process

A dialysis liquid according to the systems and methods described herein was tested by using a HepaWash® (Munich, Germany) dialysis device (Hepa Wash LK2001 dialysis device). As a reference device, a dialysis device (Nikkiso DBB-03 dialysis device) commercially offered by Nikkiso (Japan) was used.

The HepaWash® dialysis device was described previously, but not in combination with the systems and methods described herein, nor in combination with the purpose of carbon dioxide removal from blood.

The reference device commercially offered by Nikkiso is a conventional hemodialysis system. That device uses a counter-current and is thus specifically designed to provide a renal support (hemodialysis), and to remove the undesired substance urea from the blood. The device is connected directly to osmosis apparatus for supply of osmosis water. The dialysis liquid is used in a single pass process; i.e. after a single pass through the dialyzer, the dialysis liquid is discarded.

Two different dialysis liquids were used for the both devices (HepaWash® and Nikkiso). For the Nikkiso hemodialysis system a dialysis liquid with a pH of 7.45 was used, which is characterized as follows:

| | | |
|---|---|---|
| $Na^+$ | 138.00 | mmol/l |
| $K^+$ | 2.00 | mmol/l |
| $Ca^{2+}$ | 1.50 | mmol/l |
| $Mg^{2+}$ | 0.50 | mmol/l |
| $Cl^-$ | 109.00 | mmol/l |
| Acetate | 3.00 | mmol/l |
| $HCO_3^-$ | 32.00 | mmol/l |
| Glucose | 1.00 | g/l |

For the HepaWash® device a dialysis liquid with a pH of 9 was used, which is characterized as follows:

| | | |
|---|---|---|
| $Na^+$ | 138.00 | mmol/l |
| $K^+$ | 4.00 | mmol/l |
| $Ca^{2+}$ | 2.50 | mmol/l |
| $Mg^{2+}$ | 0.50 | mmol/l |
| $Cl^-$ | 110.00 | mmol/l |
| $HCO_3^-$ | 20.00 | mmol/l |
| Glucose | 1.00 | g/l |
| Albumin | 20.00 | g/l |

It was a goal of this experiment to compare these two dialysis devices. In particular, it was a goal to determine which device is capable of efficiently removing added carbon dioxide from blood. For that purpose, 110 sccm $CO_2$ was continuously added per minute to pig blood (i.e. 110 sccm $CO_2$/min). The $CO_2$-containing blood was subjected to dialysis under the following conditions:

HepaWash®:
    Blood Flow: 400 ml/min.
    Dialysis liquid flow: 800 ml/min.
Nikkiso:
    Blood Flow: 350 ml/min.
    Dialysis liquid flow: 500 ml/min.
The blood was recycled in both cases.

Figure 4:
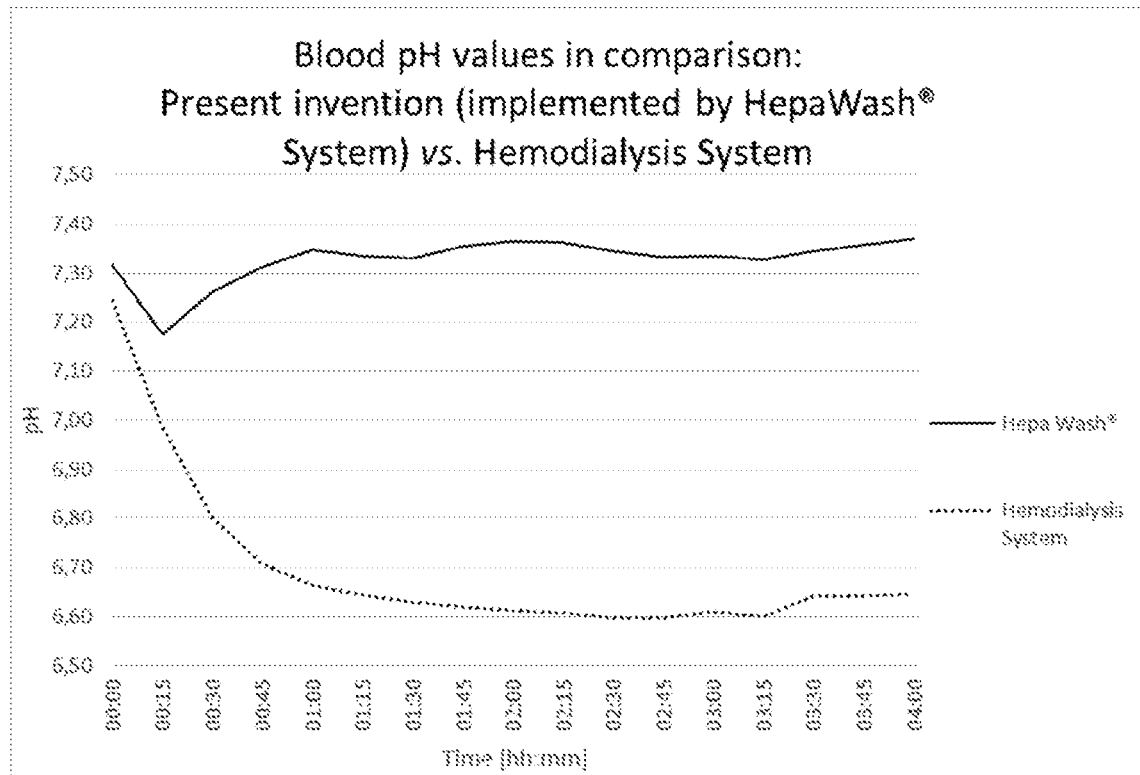
FIG. 4 exemplifies a comparison of the methods as described herein with a reference method as described in Example 2.

The result is shown in FIG. 4. The figure compares blood pH values during treatment with these different devices (Nikkiso and Hepa Wash®). As can be seen from the figure, only the Hepa Wash® system, but not the Nikkiso system (Hemodialysis System), can maintain the blood pH between 7.3 and 7.4, while the pH value of the blood treated with the Nikkiso machine (Hemodialysis System) rapidly fell to 6.65.

As can be taken from FIG. 4, renal dialysis (hemodialysis) machines, such as the one offered by Nikkiso, are incapable of preventing the problem of over-acidification of the blood. Without wishing to be bound to a particular theory, it is thought that this system removes not only $H^+$ ions, but also the buffering agent bicarbonate, from the blood. Removing $H^+$ and bicarbonate resembles the removal of $CO_2$ in the lung.

The Hepa Wash® system makes it possible to remove excess $H^+$ ions (present due to dissociation of carbonic acid into bicarbonate and $H^+$ ions). This system is therefore capable to efficiently prevent over-acidification of the blood. As indicated above, and as known to the skilled person, a blood pH values below 6.8 (over-acidification of blood) is to be avoided. This goal can be achieved with the Hepa Wash® system. On the other hand, as also shown in this example, the dialysis device by Nikkiso is not suitable for $CO_2$ removal from blood upon maintenance of blood pH.

Example 3

Calcium Concentrations

Figure 5:
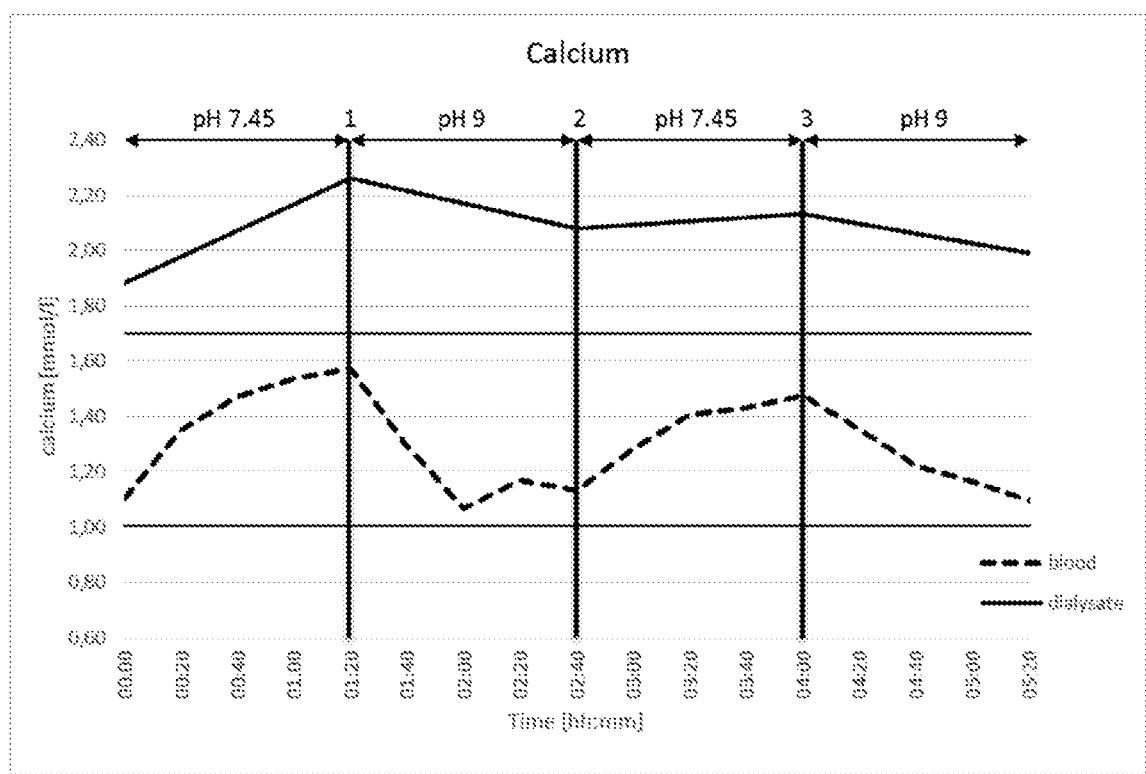
FIG. 5 shows Ca' levels in a dialysis fluid and blood over time as described in Example 3.

Dialysis liquid comprising calcium ($Ca^{2+}$ ions) was used, and the pH of the dialysis liquid was altered between pH 7.45 and pH 9 (FIG. 5). The dialysis liquid was in contact with blood across a semipermeable membrane. The calcium concentration in blood was determined. As can be seen from FIG. 5, even in the case of a calcium concentration above 1.70 mmol/l in the dialysis liquid, the calcium ion concentration in the blood remains within the desired range of 1.00-1.70 mmol/l. This demonstrates that the calcium ion concentration in the dialysis liquid according to the systems and methods described herein is suitably in a range above 1.70 mmol/l.

Experiment 4

Materials and Methods

A dialysis system (a modified HepaWash® LK2001 dialysis device (HepaWash, Munich, Germany) as described herein was provided. The HepaWash® dialysis device was described previously, but not in combination with the setup according to the present invention, nor in combination with the purpose of lactic acid removal from blood.

For the HepaWash® device a dialysis liquid was used which is characterized as follows:

| | | |
|---|---|---|
| $Na^+$ | 138.00 | mmol/l |
| $K^+$ | 4.00 | mmol/l |
| $Ca^{2+}$ | 2.50 | mmol/l |
| $Mg^{2+}$ | 0.50 | mmol/l |
| $Cl^-$ | 110.00 | mmol/l |
| $HCO_3^-$ | 20.00 | mmol/l |
| Glucose | 1.00 | g/l |
| Albumin | 20.00 | g/l |

A goal of this experiment was to compare the dialysate DiaIN 11, dialysate DiaOUT 12, blood BloodIN 9 and blood BloodOUT 10 pH. In particular, a goal was to demonstrate the correlation of the different pH values while changing the amount of added lactic acid and dialysate pH.

For that purpose five liters of pig blood were treated in the extracorporeal circuit 39 (see, FIGS. 1 and 2). The blood was subjected to dialysis under the following conditions:
Blood Flow: 400 ml/min.
Dialysis liquid flow: 800 ml/min.
The blood was continuously recycled at a temperature of 37° C.

After five minutes 3 mmol of lactic acid was continuously added per minute to pig blood (i.e., 3 mmol lactic acid/min). That is, 3 mmol per minute of lactic acid was continuously added to pig blood. After 20 minutes the blood reservoir had a pH of about 7.0 which was measured with a pH meter 9 (see, FIGS. 1 and 2). The pH of the dialysis liquid entering the dialyzer was then set to pH 9. The DiaIN value was measured by sensor 11 (see, FIGS. 1 and 2).

After 55 minutes the amount of lactic acid was decreased to 1 mmol lactic acid. So 1 mmol lactic acid was continuously added per minute to pig blood (i.e., 1 mmol lactic acid/min). That is 1 mmol per minute lactic acid was continuously added to pig blood.

As the pH of the dialysis liquid leaving the dialyzer 5 which was measured at sensor 12 increased, the pH of the dialysis liquid entering the dialyzer was decreased (see, FIGS. 1 and 2).

Results

Figure 6:
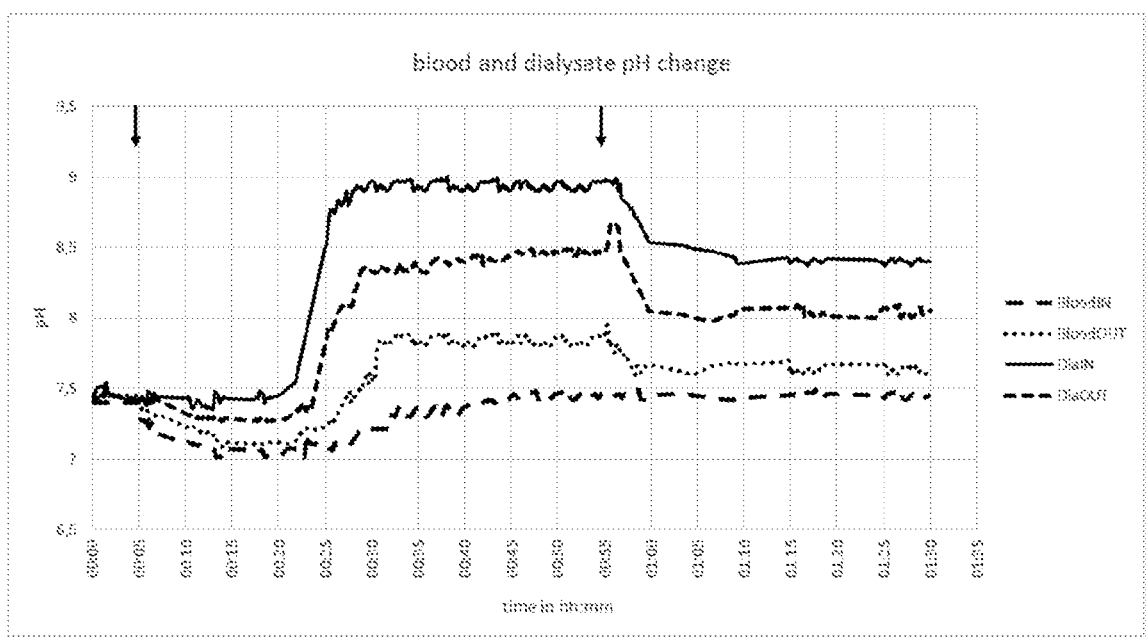
FIG. 6 shows the blood and dialysate pH values during treatment with a dialysis system as described herein (modified HepaWash® LK2001 dialysis device (HepaWash, Munich, Germany)). The blood pH can be changed while passing through the dialyzer. There is a direct correlation between the pH values of the blood and of the dialysis liquid. The dialysis device can adjust the pH of the dialysis liquid entering the dialyzer in accordance with the flow rates of both liquids entering the dialyzer.
Figure 7:
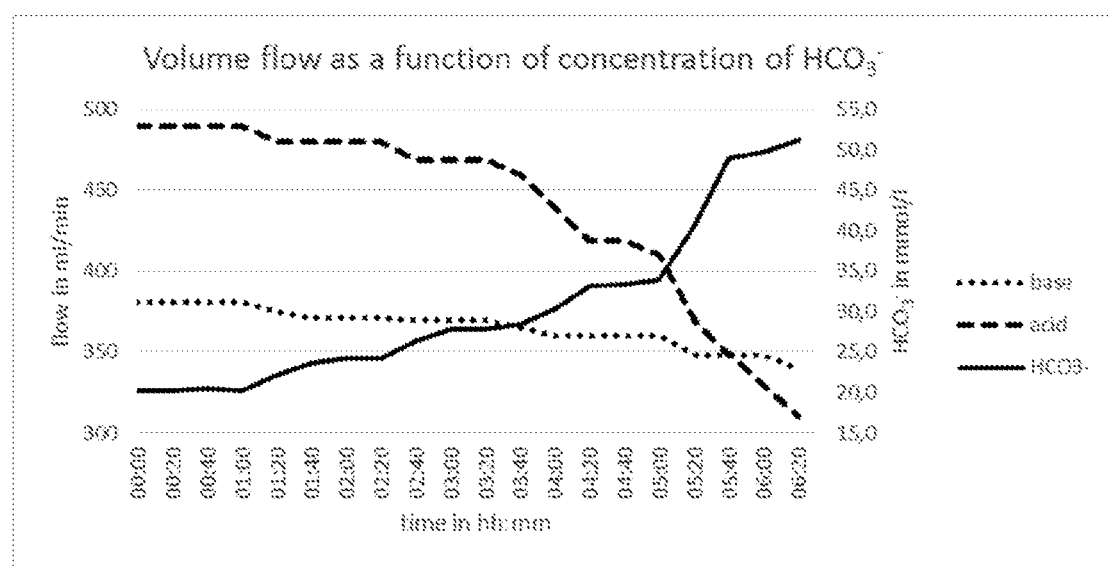
FIG. 7 shows the volume of flow through a dialysis system as described herein as a function of the concentration of $HCO_3^-$. The flow rate decreases with increasing $HCO_3^-$ concentrations (ml/min as the concentration increases mmol/l).

The result are shown in FIG. 6 that shows the blood and dialysate pH values during treatment with the dialysis devices (modified HepaWash® LK2001 dialysis device (HepaWash, Munich, Germany)). As shown in FIG. 6, the blood pH can be changed while passing through the dialyzer. There is a direct correlation between the pH values of the blood and of the dialysis liquid. The difference between the pH of the liquid entering the dialyzer and the pH of the liquid leaving the dialyzer is also in direct correlation with the liquid which is in contact through the membrane 6 (see, FIGS. 1 and 2).

Further, it is possible to calculate the amount of protons removed by knowing the buffering capacity of the dialysis liquid. A lower concentration of protons in the blood results in a smaller delta between DiaIN and DiaOUT. Hence, the dialysis device can adjust the pH of the dialysis liquid entering the dialyzer in accordance with the flow rates of both liquids entering the dialyzer. If the pH of the dialysis liquid leaving the dialyzer is smaller or is close to the pH value of the dialysis liquid entering the dialyzer, an algorithm may decrease the pH value of the dialysis liquid entering the dialyzer in accordance to the flowrates.

A dialysis system as described herein such as the Hepa Wash' system allows removing excess acid. A dialysis system as described herein such as the Hepa Wash® system is therefore capable of efficiently preventing over-acidification of the blood. As indicated above, and as known to those of ordinary skill in the art, a blood pH value below about 6.8 (over-acidified blood) is detrimental and to be avoided. A dialysis system as described herein such as the Hepa Wash® system also makes it possible to prevent a blood pH from rising to an undesirable level, such as above about 8.2. As known to those of ordinary skill in the art, a blood pH value higher than about 8.2 is harmful for blood.

We claim:

1. A method for removing hydrogen cations ($H^+$) from a biological fluid in a dialysis system comprising a dialyzer, the method comprising (a) exposing the biological fluid to a dialysis fluid across a semipermeable membrane in the dialyzer, wherein the dialysis fluid comprises (i) a pH in the range from pH 8.0 to pH 11.0, (ii) at least one buffering agent having a pKa value in the range of 7.0 to 11.0, and (iii) a buffering capacity of at least 12 mmol/l for $H^+$ ions,
  wherein the method further comprises (b) automatically quantifying the amount of hydrogen cations ($H^+$) removed from the biological fluid, wherein the amount of hydrogen cations ($H^+$) removed from the biological fluid is calculated based on the buffering capacity of the dialysis liquid and the difference of the pH of the dialysis liquid entering the dialyzer and the pH of the dialysis liquid exiting the dialyzer.

2. A method according to claim 1, wherein the automatically quantifying the amount of hydrogen cations ($H^+$) removed from the biological fluid comprises measuring the pH of the dialysis fluid prior to exposing the biological fluid to the dialysis fluid across the semipermeable membrane and measuring the pH of the dialysis fluid after contacting the biological fluid across the semipermeable membrane.

3. A method according to claim 1, wherein the dialysis fluid comprises at least one buffering agent selected from the group consisting of Tris(hydroxymethyl)aminomethane (Tris, THAM), carbonate/bicarbonate and albumin.

4. A method according to claim 1, further comprising (c) treating the dialysis fluid by exposing the dialysis fluid to one or more of (i) an adsorber, (ii) a membrane, (iii) an acidic pH, and (iv) a basic pH.

5. A method according to claim 4 wherein (c) treating the dialysis fluid comprises removing carbon dioxide, $H^+$ or $HCO_3^-$ from the dialysis fluid.

6. A method according to claim 1, further comprising (d) recycling the dialysis fluid.

7. A method for extracorporeally treating blood from a human or animal subject in a dialysis system comprising a dialyzer, the method comprising:
  (a) withdrawing blood from the vein or artery of the subject;
  (b) exposing the blood to a dialysis fluid across a semipermeable membrane in the dialyzer, wherein the dialysis fluid comprises (i) a pH in the range from pH 8.0 to pH 11.0, (ii) at least one buffering agent having a pKa value in the range of 7.0 to 11.0, and (iii) a buffering capacity of at least 12 mmol/l for $H^+$ ions;
  (c) removing hydrogen cations ($H^+$) from the blood;
  (d) returning the blood to the subject; and
  (e) automatically quantifying the amount of hydrogen cations ($H^+$) removed from the blood wherein the amount of hydrogen cations ($H^+$) removed from the biological fluid is calculated based on the buffering capacity of the dialysis liquid and the difference of the pH of the dialysis liquid entering the dialyzer and the pH of the dialysis liquid exiting the dialyzer.

8. A method according to claim 7, wherein the automatically quantifying the amount of hydrogen cations ($H^+$) from the blood comprises measuring the pH of the dialysis fluid prior to exposing the blood to the dialysis fluid across the semipermeable membrane and measuring the pH of the dialysis fluid after contacting the blood across the semipermeable membrane.

9. A method according to claim 7, wherein the dialysis fluid comprises at least one buffering agent selected from the group consisting of Tris(hydroxymethyl)aminomethane (Tris, THAM), carbonate/bicarbonate and albumin.

10. A method according to claim 7, further comprising (f) treating the dialysis fluid by exposing the dialysis fluid to one or more of (i) an adsorber, (ii) a membrane, (iii) an acidic pH, and (iv) a basic pH.

11. A method according to claim 10 wherein (f) treating the dialysis fluid comprises removing carbon dioxide, $H^+$ or $HCO_3^-$ from the dialysis fluid.

12. A method according to claim 7, further comprising (g) recycling the dialysis fluid.

13. A method of treating a subject suffering from an acid/base imbalance comprising:
  (a) withdrawing a biological fluid from the subject;
  (b) exposing the biological fluid to a dialysis fluid across a semipermeable membrane in a dialyzer, wherein the dialysis fluid comprises (i) a pH in the range from pH 8.0 to pH 11.0, (ii) at least one buffering agent having a pKa value in the range of 7.0 to 11.0, and (iii) a buffering capacity of at least 12 mmol/l for $H^+$ ions;
  (c) removing hydrogen cations ($H^+$) from the biological fluid;
  (d) returning the biological fluid to the subject; and
  (e) automatically quantifying the amount of hydrogen cations ($H^+$) removed from the blood wherein the amount of hydrogen cations ($H^+$) removed from the biological fluid is calculated based on the buffering capacity of the dialysis liquid and the difference of the pH of the dialysis liquid entering the dialyzer and the pH of the dialysis liquid exiting the dialyzer.

14. A method according to claim 13, wherein the automatically quantifying the amount of hydrogen cations ($H^+$) removed from the biological fluid comprises measuring the pH of the dialysis fluid prior to exposing the biological fluid to the dialysis fluid across the semipermeable membrane and measuring the pH of the dialysis fluid after contacting the biological fluid across the semipermeable membrane.

15. A method according to claim 13, wherein the dialysis fluid comprises at least one buffering agent selected from the group consisting of Tris(hydroxymethyl)aminomethane (Tris, THAM), carbonate/bicarbonate and albumin.

16. A method according to claim 13, further comprising (f) treating the dialysis fluid by exposing the dialysis fluid to one or more of (i) an adsorber, (ii) a membrane, (iii) an acidic pH, and (iv) a basic pH.

17. A method according to claim 16 wherein (f) treating the dialysis fluid comprises removing carbon dioxide, $H^+$ or $HCO_3^-$ from the dialysis fluid.

18. A method according to claim 13, further comprising (g) recycling the dialysis fluid.

19. The method according to claim 1, wherein the buffering capacity of the dialysis fluid is determined by continuously titrating the dialysis fluid with an acid or base solution.

* * * * *